(12) United States Patent
Sigg et al.

(10) Patent No.: US 11,945,859 B2
(45) Date of Patent: Apr. 2, 2024

(54) PROTEIN SOLUTION FORMULATION CONTAINING HIGH CONCENTRATION OF AN ANTI-VEGF ANTIBODY

(71) Applicant: Novartis AG, Basel (CH)

(72) Inventors: Juergen Sigg, Loerrach (DE); Pamela De Moor, Palo Alto, CA (US)

(73) Assignee: NOVARTIS AG, Basel (CH)

(*) Notice: Subject to any disclaimer, the term of this patent is extended or adjusted under 35 U.S.C. 154(b) by 399 days.

(21) Appl. No.: 16/715,580

(22) Filed: Dec. 16, 2019

(65) Prior Publication Data

US 2020/0190179 A1 Jun. 18, 2020

Related U.S. Application Data

(60) Provisional application No. 62/781,003, filed on Dec. 18, 2018.

(51) Int. Cl.
| | | |
|---|---|---|
| *A61K 39/395* | (2006.01) | |
| *A61K 9/00* | (2006.01) | |
| *A61K 47/26* | (2006.01) | |
| *C07K 16/22* | (2006.01) | |

(52) U.S. Cl.
CPC ............ *C07K 16/22* (2013.01); *A61K 9/0048* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 6,267,958 B1 | 7/2001 | Andya et al. | |
| 8,293,235 B2 | 10/2012 | Borras et al. | |
| 8,349,322 B2 | 1/2013 | Borras et al. | |
| 8,673,310 B2 | 3/2014 | Borras et al. | |
| 8,937,162 B2 | 1/2015 | Borras et al. | |
| 9,090,684 B2 | 7/2015 | Borras et al. | |
| 9,422,366 B2 | 8/2016 | Borras et al. | |
| 9,593,161 B2 | 3/2017 | Borras et al. | |
| 9,873,737 B2 | 1/2018 | Borras et al. | |
| 10,035,850 B2 | 7/2018 | Gekkieva et al. | |
| 10,087,244 B2 | 10/2018 | Borras et al. | |
| 10,100,111 B2 | 10/2018 | Borras et al. | |
| 10,590,193 B2 | 3/2020 | Borras et al. | |
| 10,689,438 B2 * | 6/2020 | Zhang .................. | C07K 16/22 |
| 11,098,110 B2 | 8/2021 | Gekkieva et al. | |
| 2006/0088523 A1 * | 4/2006 | Andya .................. | C07K 16/32 |
| | | | 424/133.1 |
| 2013/0004484 A1 | 1/2013 | Demeule et al. | |
| 2014/0004131 A1 | 1/2014 | Mueller et al. | |
| 2014/0186373 A1 | 7/2014 | Cosenza et al. | |
| 2016/0340420 A1 * | 11/2016 | Zhang .................. | A61K 9/0048 |
| 2018/0127493 A1 | 5/2018 | Borras et al. | |
| 2018/0371074 A1 | 12/2018 | Borras et al. | |
| 2020/0172608 A1 | 6/2020 | Borras et al. | |
| 2020/0270336 A1 | 8/2020 | Zhang et al. | |
| 2021/0017266 A1 | 1/2021 | Racine et al. | |
| 2021/0340242 A1 | 11/2021 | Gekkieva et al. | |

FOREIGN PATENT DOCUMENTS

| | | |
|---|---|---|
| WO | WO2009/155724 A2 | 12/2009 |
| WO | 2012171982 A1 | 12/2012 |
| WO | 2013186700 A1 | 12/2013 |
| WO | 2014005728 A1 | 1/2014 |
| WO | 2015166112 A1 | 11/2015 |
| WO | 2016073915 A1 | 5/2016 |
| WO | WO2016073918 A1 | 5/2016 |
| WO | WO2016085750 A1 | 6/2016 |

OTHER PUBLICATIONS

Clinical Trial NCT04597632 publication dated Oct. 22, 2020, available at http://clinicaltrials.gov.
Clinical Trial NCT04543331 publication dated Sep. 10, 2020 available at http://clinicaltrials.gov.
Clinical Trial NCT04047472 publication dated Aug. 6, 2019 available at http://clinicaltrials.gov.
Clinical Trial NCT04679935 publication dated Feb. 2, 2021 available at http://clinicaltrials.gov.
Clinical Trial NCT04662944 publication dated Feb. 10, 2021 available at http://clinicaltrials.gov.
Clinical Trial NCT04287348 publication dated Aug. 14, 2021 available at http://clinicaltrials.gov.
Delphine Steyaert, "Cleaning Validation of Biologicals: Determination of a Worst-Case Product for RTH 258," Master's Thesis Paper (2016-2017), 82 pages.
Yanan et al., "Monoclonal antibodies: formulations of marketed products and recent advances in novel delivery system," Drug Development and Industrial Pharmacy, 43(4):519-530, 2017.
Sgoutas et al, Effect of Lyophilization on Determinations of Lipoprotie(a), Serum. Clin. Chem., vol. 38, No. 7, pp. 1355-1360, 1992.
Wang, Lyophilization and development of solid protein pharmaceuticals, International Journal of Pharmaceutics, vol. 203, pp. 1-60, 2000.
Daugherty, et al, "Formulation and delivery issues for monoclonal antibody therapeutics", Advanced Drug Delivery Reviews, 58, pp. 686-706 (2006).
Wang et al, "Antibody Structure, Instability, and Formulation", Journal of Pharmaceutical Sciences, vol. 96, No. 1, pp. 1-26 (2007).
Gauareault et al., Investigative Ophthalmology and Visual Science, vol. 53, Issue 14, Mar. 2012.

(Continued)

*Primary Examiner* — Yunsoo Kim
(74) *Attorney, Agent, or Firm* — Xinsong Xu

(57) ABSTRACT

The present invention provides anti-VEGF antibodies formulated as high concentration, aqueous pharmaceutical compositions, suitable for an injection, preferably an intravitreal injection. The aqueous pharmaceutical compositions are useful for delivery of a high concentration of the antibody active ingredient to a patient without high levels of antibody aggregation and without a high level of sub-visible particulate matter. An aqueous composition of the invention comprises an antibody having a concentration of at least 50 mg/ml. An aqueous pharmaceutical composition of the invention includes a sugar, a buffering agent, and a surfactant.

10 Claims, 1 Drawing Sheet
Specification includes a Sequence Listing.

(56) References Cited

OTHER PUBLICATIONS

U.S. Pharmacopeial Convention (USP) General Chapter <789> (2012).
Tolentino et al, "Drugs in Phase II clinical trials for the treatment of age-related macular degeneration", Expert Opinion on Investigational Drugs, UK, (Sep. 22, 2014), vol. 24, No. 2, pp. 183-199, 2015.
"Monthly and As-Needed Treatment in the SHORE Study Resulted in Similar Visual Activity Gains in RVO", Retina today, (Sep. 1, 2014), pp. 14-17, Sep. 2014: URL: http://retinatoday.com/pdfs/rt0914_ASRS wrap up.pdf , (Apr. 6, 2016).
Pravin Dugel, "Novel molecule shows promise for future treatment of neovascular AMD", ASRS, 2014, San Diego, (Aug. 11, 2014); URL: http://www.healio.com/ophthalmology/retina-vitreous/news/online/%7B7ad33cbd-a2e0-49f1-a3f6-00fa79715708%7D/novel-molecule-shows-promise-for-future-treatment-ofneovascular-amd, (Apr. 6, 2016).
Jeffrey S Heier, "Intravitreal Aflibercept for AMD: 2-year Results", Retina Today, (Mar. 1, 2012), pp. 49-51; URL: http://retinatoday.com/pdfs/rt0312_feature_heier.pdf, (Apr. 6, 2016).
Pravin Dugel, "Results of ESBA 1008, a Single-Chain Antibody Fragment, for the Treatment of Neovascular AMD", URL:http://eyetube.net/series/daily-coverage-san-diego-august2014/asile/, (Apr. 11, 2016), Video Only.
Dugel et al., "Hawk and Harrier: Phase 3, Multicenter, Randomized, Double-Masked Trials of Brolucizumab for Neovascular Age-Related Macular Degeneration", American Academy of Ophthalmology, vol. 127, No. 1, Jan. 2020.
Yannuzzi et al., "Brolucizumab: evidence to date in the treatment of neovascular age-related macular degeneration", Clinical Ophthalmology, vol. 13, pp. 1323-1329, 2019.
U.S. Appl. No. 13/000,423.
U.S. Appl. No. 13/708,575.
U.S. Appl. No. 14/741,430.
U.S. Appl. No. 15/814,784.
U.S. Appl. No. 16/779,028.
U.S. Appl. No. 14/934,731.
U.S. Appl. No. 16/018,244.
U.S. Appl. No. 14/934,666.
NCT01796964.
NCT01304693.
NCT01849692.
NCT02434328.
NCT02307682.
NCT02507388.
NCT03954626.
NCT04264819.
NCT04239027.
NCT03930641.
NCT04005352.
NCT04278417.
NCT04058067.
NCT03710564.
NCT03386474.
NCT04079231.
NCT03917472.
NCT03481660.
NCT03481634.
NCT03810313.
NCT03802630.
Clinical Trial NCT05112835, Nov. 9, 2021, available at https://www.clinicaltrials.gov/ct2/show/NCT05112835 (9 pages).
Tyagi, et al., The use of chemical modification and chemical cross-linking for the stabilization of proteins (enzymes), Biochemistry, 1998, 395-407, 63(3) (English abstract provided).
State Pharmacopoeia of the Russian Federation, Rules for the use of pharmacopoeial monographs, 2018, XIV edition, pp. 122-127, URL: http://pharmacopeia.ru/c1d4da043aaaefd5915a91c35d831536125.html, vol. 1, Moscow.
Oganov et al., The importance of evidence medicine for clinical practice, Fundamentals of Evidence Medicine textbook, 2010, 136, Silitseya-Poligraf, Moscow.
Mandal, et al., Ocular delivery of proteins and peptides: Challenges and novel formulation approaches, Advanced Drug Delivery Reviews, Jan. 13, 2018, 67-95, 126.
Clinical Trial NCT04597632, Oct. 22, 2020, available at https://clinicaltrials.gov/ct2/show/NCT04597632?term=NCT04597632&draw=2&rank=1(8 pages).
Clinical Trial NCT04543331, Sep. 10, 2020, available at https://clinicaltrials.gov/ct2/show/NCT04543331?term=NCT04543331&draw=2&rank=1(8 pages).
Clinical Trial NCT04047472, Aug. 6, 2019, available at https://clinicaltrials.gov/ct2/show/NCT04047472?term=NCT04047472&draw=2&rank=1(12 pages).
Clinical Trial NCT04679935, Dec. 22, 2020 available at hhttps://clinicaltrials.gov/ct2/show/NCT04679935?term=NCT04679935&draw=2&rank=1(11 pages).
Clinical Trial NCT04662944,, Dec. 10, 2020 available at https://clinicaltrials.gov/ct2/show/NCT04662944?term=NCT04662944&draw=2&rank=1(9 pages).
Clinical Trial NCT04287348 ,Feb. 27, 2020 available at https://clinicaltrials.gov/ct2/show/NCT04287348?term=NCT04287348&draw=2&rank=1(9 pages).
Clinical Trial NCT01796964, Feb. 22, 2013 available at https://clinicaltrials.gov/ct2/show/NCT01796964?term=NCT01796964&draw=2&rank=1(8 pages).
Clinical Trial NCT01304693, Feb. 25, 2011 available at https://clinicaltrials.gov/ct2/show/NCT01304693?term=NCT01304693&draw=2&rank=1(6 pages).
Clinical Trial NCT01849692, May 8, 2013 available at https://clinicaltrials.gov/ct2/show/NCT01849692?term=NCT01849692&draw=2&rank=1(8 pages).
Clinical Trial NCT02434328, May 5, 2015, available at https://clinicaltrials.gov/ct2/show/NCT02434328?term=NCT02434328&draw=2&rank=1 (15 pages).
Clinical Trial NCT02307682, Dec. 4, 2014, available at https://clinicaltrials.gov/ct2/show/NCT02307682?term=NCT02307682&draw=2&rank=1 (16 pages).
Clinical Trial NCT02507388, Jul. 23, 2015, available at https://clinicaltrials.gov/ct2/show/NCT02507388?term=NCT02507388&draw=2&rank=1 (8 pages).
Clinical Trial NCT03954626, May 17, 2019 available at https://clinicaltrials.gov/ct2/show/NCT03954626?term=NCT03954626&draw=2&rank=1 (8 pages).
Clinical Trial NCT04264819, Feb. 11, 2020 available at https://clinicaltrials.gov/ct2/show/NCT04264819?term=NCT04264819&draw=2&rank=1 (9 pages).
Clinical Trial NCT04239027, Jan. 23, 2020, available at https://clinicaltrials.gov/ct2/show/NCT04239027?term=NCT04239027&draw=2&rank=1 (12 pages).
Clinical Trial NCT03930641, Apr. 29, 2019, available at https://clinicaltrials.gov/ct2/show/NCT03930641?term=NCT03930641&draw=2&rank=1(7 pages).
Clinical Trial NCT04005352, Jul. 2, 2019, available at https://clinicaltrials.gov/ct2/show/NCT04005352?term=NCT04005352&draw=2&rank=1 (8 pages).
Clinical Trial NCT04278417, Feb. 20, 2020, available at https://clinicaltrials.gov/ct2/show/NCT04278417?term=NCT04278417&draw=2&rank=1 (7 pages).
Clinical Trial NCT04058067, Aug. 15, 2019, available at https://clinicaltrials.gov/ct2/show/NCT04058067?term=NCT04058067&draw=2&rank=1 (11 pages).
Clinical Trial NCT03710564, Oct. 18, 2018, available at https://clinicaltrials.gov/ct2/show/NCT03710564?term=NCT03710564&draw=2&rank=1 (11 pages).
Clinical Trial NCT03386474, Dec. 29, 2017, available at https://clinicaltrials.gov/ct2/show/NCT03386474?term=NCT03386474&draw=2&rank=1(9 pages).
Clinical Trial NCT04079231, Sep. 6, 2019, available at https://clinicaltrials.gov/ct2/show/NCT04079231?term=NCT04079231&draw=2&rank=1 (9 pages).

(56) References Cited

OTHER PUBLICATIONS

Clinical Trial NCT03917472, Apr. 17, 2019, available at https://clinicaltrials.gov/ct2/show/NCT03917472?term=NCT03917472&draw=2&rank=1 (11 pages).
Clinical Trial NCT03481660, Mar. 29, 2018, available at https://clinicaltrials.gov/ct2/show/NCT03481660?term=NCT03481660&draw=2&rank=1 (10 pages).
Clinical Trial NCT03481634, Mar. 29, 2018, available at https://clinicaltrials.gov/ct2/show/NCT03481634?term=NCT03481634&draw=2&rank=1 (17 pages).
Clinical Trial NCT03810313, Jan. 8, 2019 available at https://clinicaltrials.gov/ct2/show/NCT03810313?term=NCT03810313&draw=2&rank=1 (12 pages).
Clinical Trial NCT03802630, Jan. 14, 2019 available at https://clinicaltrials.gov/ct2/show/NCT03802630?term=NCT03802630&draw=2&rank=1 (12 pages).
Steyaert, Cleaning Validation of Biologicals: Determination of a Worse-Case Product for RTH 258, Master's Thesis Paper (2016-2017), 82 pages.
U.S. Appl. No. 17/641,799, filed Mar. 9, 2022.
Chen, et al., The influences of additives on the stability of interferon alfa in liquid state, Chinese Journal of New Drugs, 2008, 1425-1428, 17(16).
Mason, et al. "Effect of pH and Light on Aggregation and Conformation of an IgG1 mAb," Mol. Pharmaceuticals, 9, 774-790, 2012.
Wuchner et al., "Industry Perspective ont the use and Characterization of Polysorbates for Biopharmaceutical Products Part 1: Survey Report on Current State and Common Practices for Handling and Control of Polysorbates," Journal of Pharmaceutical Sciences, 111, 1280-1291, 2022.
Usach, et al. "Subcutaneous Injection of Drugs: Literature Review of Factors Influencing Pain Sensation at the Injection Site," Adv. Ther., 36:2986-2996, 2019.
Srivastava, et al. "Approaches to Alleviating Subcutaneous Injection-Ste Pain for Citrate Formulations," Pharmaceutical Technology, 32-37, Jun. 2020.
Agarkhed, et al. "Effect of Polysorbate 80 Concentration on Thermal and Photostability of a Monoclonal Antibody," AAPS PharmaSciTech, Vo. 14, No. 1, 1-9, Mar. 2013.
Desai, et al. "An Intercompany Perpective on Practical Experiences of Predicting, Optimizing and Analyzing High Concentration Biologic Therapeutic Formulations," 112, 359-369, 2023.
Beovu label, "Highlights of prescribing information," Initial U.S. Approval: 2019, revised Dec. 2022, 15 pages.
U.S. Appl. No. 16/871,765.

* cited by examiner

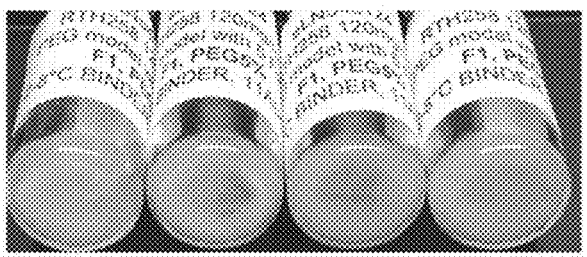
F1
F2
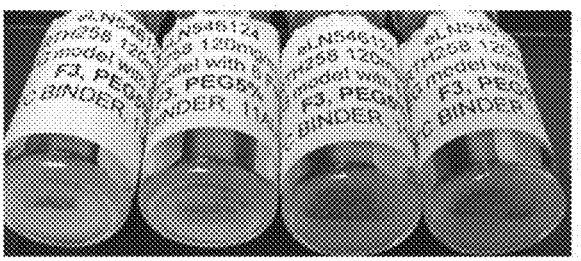
F3
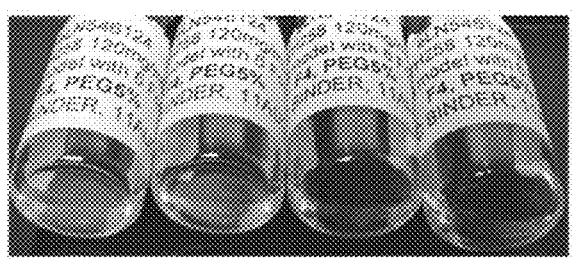
F4
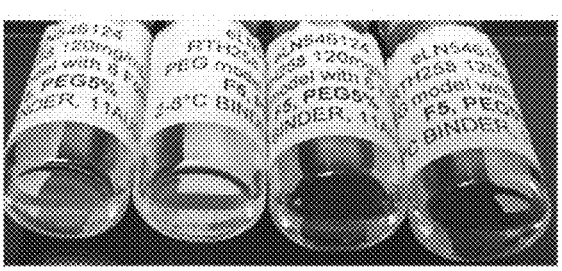
F5
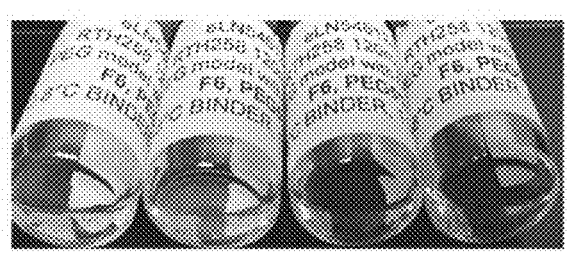
F6

SEQUENCE LISTING

<160> NUMBER OF SEQ ID NOS: 10

<210> SEQ ID NO 1
<211> LENGTH: 120
<212> TYPE: PRT
<213> ORGANISM: Artificial Sequence
<220> FEATURE:
<223> OTHER INFORMATION: synthetic peptide

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Thr Asp Tyr
            20                  25                  30

Tyr Tyr Met Thr Trp Val Arg Gln Ala Pro Gly Lys Gly Leu Glu Trp
        35                  40                  45

Val Gly Phe Ile Asp Pro Asp Asp Pro Tyr Tyr Ala Thr Trp Ala
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Gly Gly Asp His Asn Ser Gly Trp Gly Leu Asp Ile Trp Gly Gln
            100                 105                 110

Gly Thr Leu Val Thr Val Ser Ser
        115                 120

<210> SEQ ID NO 2
<211> LENGTH: 111
<212> TYPE: PRT
<213> ORGANISM: Artificial Sequence
<220> FEATURE:
<223> OTHER INFORMATION: synthetic peptide

<400> SEQUENCE: 2

Glu Ile Val Met Thr Gln Ser Pro Ser Thr Leu Ser Ala Ser Val Gly
1               5                   10                  15

Asp Arg Val Ile Ile Thr Cys Gln Ala Ser Glu Ile Ile His Ser Trp
            20                  25                  30

Leu Ala Trp Tyr Gln Gln Lys Pro Gly Lys Ala Pro Lys Leu Leu Ile
        35                  40                  45

Tyr Leu Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Val Tyr Leu Ala Ser Thr
                85                  90                  95

Asn Gly Ala Asn Phe Gly Gln Gly Thr Lys Leu Thr Val Leu Gly
            100                 105                 110

<210> SEQ ID NO 3
<211> LENGTH: 251
<212> TYPE: PRT
<213> ORGANISM: Artificial Sequence
<220> FEATURE:
<223> OTHER INFORMATION: synthetic peptide

<400> SEQUENCE: 3

Glu Ile Val Met Thr Gln Ser Pro Ser Thr Leu Ser Ala Ser Val Gly
1               5                   10                  15

Asp Arg Val Ile Ile Thr Cys Gln Ala Ser Glu Ile Ile His Ser Trp
            20                  25                  30

Leu Ala Trp Tyr Gln Gln Lys Pro Gly Lys Ala Pro Lys Leu Leu Ile
        35                  40                  45

Tyr Leu Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Val Tyr Leu Ala Ser Thr
                85                  90                  95

Asn Gly Ala Asn Phe Gly Gln Gly Thr Lys Leu Thr Val Leu Gly Gly
            100                 105                 110

Gly Gly Gly Ser Gly Gly Gly Gly Ser Gly Gly Gly Ser Gly Gly
        115                 120                 125

Gly Gly Ser Glu Val Gln Leu Val Glu Ser Gly Gly Gly Leu Val Gln
        130                 135                 140
```

```
Pro Gly Gly Ser Leu Arg Leu Ser Cys Thr Ala Ser Gly Phe Ser Leu
145                 150                 155                 160

Thr Asp Tyr Tyr Tyr Met Thr Trp Val Arg Gln Ala Pro Gly Lys Gly
                165                 170                 175

Leu Glu Trp Val Gly Phe Ile Asp Pro Asp Asp Pro Tyr Tyr Ala
            180                 185                 190

Thr Trp Ala Lys Gly Arg Phe Thr Ile Ser Arg Asp Asn Ser Lys Asn
            195                 200                 205

Thr Leu Tyr Leu Gln Met Asn Ser Leu Arg Ala Glu Asp Thr Ala Val
    210                 215                 220

Tyr Tyr Cys Ala Gly Gly Asp His Asn Ser Gly Trp Gly Leu Asp Ile
225                 230                 235                 240

Trp Gly Gln Gly Thr Leu Val Thr Val Ser Ser
                245                 250

<210> SEQ ID NO 4
<211> LENGTH: 252
<212> TYPE: PRT
<213> ORGANISM: Artificial Sequence
<220> FEATURE:
<223> OTHER INFORMATION: synthetic peptide

<400> SEQUENCE: 4

Met Glu Ile Val Met Thr Gln Ser Pro Ser Thr Leu Ser Ala Ser Val
1               5                   10                  15

Gly Asp Arg Val Ile Ile Thr Cys Gln Ala Ser Glu Ile Ile His Ser
            20                  25                  30

Trp Leu Ala Trp Tyr Gln Gln Lys Pro Gly Lys Ala Pro Lys Leu Leu
        35                  40                  45

Ile Tyr Leu Ala Ser Thr Leu Ala Ser Gly Val Pro Ser Arg Phe Ser
    50                  55                  60

Gly Ser Gly Ser Gly Ala Glu Phe Thr Leu Thr Ile Ser Ser Leu Gln
65                  70                  75                  80

Pro Asp Asp Phe Ala Thr Tyr Tyr Cys Gln Asn Val Tyr Leu Ala Ser
                85                  90                  95

Thr Asn Gly Ala Asn Phe Gly Gln Gly Thr Lys Leu Thr Val Leu Gly
            100                 105                 110

Gly Gly Gly Gly Ser Gly Gly Gly Ser Gly Gly Gly Gly Ser Gly
        115                 120                 125

Gly Gly Gly Ser Glu Val Gln Leu Val Glu Ser Gly Gly Gly Leu Val
130                 135                 140

Gln Pro Gly Gly Ser Leu Arg Leu Ser Cys Thr Ala Ser Gly Phe Ser
145                 150                 155                 160

Leu Thr Asp Tyr Tyr Tyr Met Thr Trp Val Arg Gln Ala Pro Gly Lys
                165                 170                 175

Gly Leu Glu Trp Val Gly Phe Ile Asp Pro Asp Asp Pro Tyr Tyr
            180                 185                 190

Ala Thr Trp Ala Lys Gly Arg Phe Thr Ile Ser Arg Asp Asn Ser Lys
        195                 200                 205

Asn Thr Leu Tyr Leu Gln Met Asn Ser Leu Arg Ala Glu Asp Thr Ala
    210                 215                 220

Val Tyr Tyr Cys Ala Gly Gly Asp His Asn Ser Gly Trp Gly Leu Asp
225                 230                 235                 240

Ile Trp Gly Gln Gly Thr Leu Val Thr Val Ser Ser
                245                 250
```

<210> SEQ ID NO 5
<211> LENGTH: 11
<212> TYPE: PRT
<213> ORGANISM: Artificial Sequence
<220> FEATURE:
<223> OTHER INFORMATION: synthetic peptide

<400> SEQUENCE: 5

Gly Phe Ser Leu Thr Asp Tyr Tyr Tyr Met Thr
1               5                   10

<210> SEQ ID NO 6
<211> LENGTH: 16
<212> TYPE: PRT
<213> ORGANISM: Artificial Sequence
<220> FEATURE:
<223> OTHER INFORMATION: synthetic peptide

<400> SEQUENCE: 6

Phe Ile Asp Pro Asp Asp Pro Tyr Tyr Ala Thr Trp Ala Lys Gly
1               5                   10                  15

<210> SEQ ID NO 7
<211> LENGTH: 11
<212> TYPE: PRT
<213> ORGANISM: Artificial Sequence
<220> FEATURE:
<223> OTHER INFORMATION: synthetic peptide

<400> SEQUENCE: 7

Gly Asp His Asn Ser Gly Trp Gly Leu Asp Ile
1               5                   10

<210> SEQ ID NO 8
<211> LENGTH: 11
<212> TYPE: PRT
<213> ORGANISM: Artificial Sequence
<220> FEATURE:
<223> OTHER INFORMATION: synthetic peptide

<400> SEQUENCE: 8

Gln Ala Ser Glu Ile Ile His Ser Trp Leu Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: synthetic peptide

<400> SEQUENCE: 9

Leu Ala Ser Thr Leu Ala Ser
1               5

<210> SEQ ID NO 10
<211> LENGTH: 12
<212> TYPE: PRT
<213> ORGANISM: Artificial Sequence
<220> FEATURE:
<223> OTHER INFORMATION: synthetic peptide

<400> SEQUENCE: 10

Gln Asn Val Tyr Leu Ala Ser Thr Asn Gly Ala Asn
1               5                   10

PROTEIN SOLUTION FORMULATION CONTAINING HIGH CONCENTRATION OF AN ANTI-VEGF ANTIBODY

SEQUENCE LISTING

The instant application contains a Sequence Listing which has been submitted electronically in ASCII format and is hereby incorporated by reference in its entirety. Said ASCII copy, created on Dec. 11, 2019, is named PAT058325_sequence_listing_2019_ST25.txt and is 9 KB in size.

FIELD OF THE INVENTION

The present invention relates to aqueous pharmaceutical formulations of anti-VEGF antibodies, a process for the preparation thereof, and uses of the formulations.

BACKGROUND OF THE INVENTION

Vascular endothelial growth factor (VEGF) is a known regulator of angiogenesis and neovascularization, and has been shown to be a key mediator of neovascularization associated with tumors and intraocular disorders (Ferrara et al. Endocr. Rev. 18:4-25 (1997)). The VEGF mRNA is overexpressed in many human tumors, and the concentration of VEGF in eye fluids are highly correlated to the presence of active proliferation of blood vessels in patients with diabetic and other ischemia-related retinopathies (Berkman et al., J Clin Invest 91:153-159 (1993); Brown et al. Human Pathol. 26:86-91 (1995); Brown et al. Cancer Res. 53:4727-4735 (1993); Mattern et al. Brit. J. Cancer. 73:931-934 (1996); and Dvorak et al. Am J. Pathol. 146:1029-1039 (1995); Aiello et al. N. Engl. J. Med. 331:1480-1487 (1994)). In addition, recent studies have shown the presence of localized VEGF in choroidal neovascular membranes in patients affected by AMD (Lopez et al. Invest. Ophtalmo. Vis. Sci. 37:855-868 (1996)). Anti-VEGF neutralizing antibodies can be used to suppress the growth of a variety of human tumor cell lines in nude mice and also inhibit intraocular angiogenesis in models of ischemic retinal disorders (Kim et al. Nature 362:841-844 (1993); Warren et al. J. Clin. Invest 95:1789-1797 (1995); Borgstrom et al. Cancer Res. 56:4032-4039 (1996); and Melnyk et al. Cancer Res. 56:921-924 (1996)) (Adamis et al. Arch. Opthalmol. 114: 66-71 (1996)).

A number of antibodies are approved for therapeutic use in humans and other mammals, including anti-VEGF antibodies. The concentration of therapeutic antibodies in liquid pharmaceutical formulations varies widely depending, for example, on the route of administration. There is often a need for a high concentration formulation of an antibody when small volumes are desired. For example, high concentration formulations may be desirable for intravitreal injection or subcutaneous administration.

However, formulations with high concentration of antibody may have short shelf lives, and the formulated antibodies may lose biological activity caused by chemical and physical instabilities during storage. Aggregation, deamidation and oxidation are known to be the most common causes of antibody degradation. In particular, aggregation can potentially lead to increased immune response in patients, leading to safety concerns. Thus it must be minimized or prevented.

Formation of particulates in biotherapeutic formulations is also a major quality concern, as particulates in the tens of microns to sub-millimeter and millimeter size range can generally be seen by the naked human eye (see Das, 2012, *AAPS PharmSciTech,* 13:732-746). Particulates in therapeutic ophthalmic preparations, even those which can be seen only by microscope or light obscuration, can cause damage to the eye. Therefore, there are regulatory standards to ensure sub-visible particulate matter content in ophthalmic formulations is within certain limits. For example, the U.S. Pharmacopeial Convention (USP) has set requirements for particulate matter in ophthalmic solutions, such as the maximum number of particles ≥10 μm diameter is 50 per mL, the maximum number of particles ≥25 μm diameter is 5 per mL, and the maximum number of particles ≥50 μm diameter is 2 per mL determined by the microscopic or light obscuration method particle count (see USP General Chapter <789>).

Methods for producing high concentration antibody formulations are known. However, a universal approach does not exist to overcome the unpredictable impact of an antibody's amino acid sequence on its tendency to form aggregates or degrade in the presence of various pharmaceutical excipients, buffers, etc. Further, preparing an ophthalmic formulation with a high concentration of protein (such as an antibody) that contains an acceptable level of sub-visible particles is challenging and not predictable. Development of formulations for protein drugs requiring high dosing is challenging for solubility limited proteins and also results in several manufacturing, stability, analytical, and delivery challenges. The concentration dependent degradation route of aggregation is the greatest challenge to developing protein formulations at these higher concentrations. In addition to the potential for non-native protein aggregation and particulate formation, reversible self-association may occur, which contributes to properties such as viscosity that complicates delivery by injection. In addition, aqueous protein formulations may become cloudy and turbid over time as they are stored, for example in a refrigerator or freezer. Cloudiness and turbidity is generally associated with aggregation or crystallization of the proteins in the formulation. There is a strong preference to avoid any cloudiness or turbidity in a protein formulation to avoid any need for filtration or other means of clarifying the formulation before injection or otherwise delivering it to the patient.

It is an object of the invention to provide further and improved formulations with high concentration of anti-VEGF antibodies and low levels of antibody aggregation and sub-visible particles, that are suitable for administration to a human, in particular to a human eye, and which avoid cloudiness/turbidity/crystallization.

SUMMARY OF THE INVENTION

Accordingly, the present invention is directed to an aqueous pharmaceutical composition comprising a high concentration of anti-VEGF antibody suitable for ophthalmic injection. In certain aspects, the aqueous pharmaceutical compositions of the invention exhibit low to undetectable levels of antibody aggregation or degradation, with very little to no loss of the biological activities during manufacture, preparation, transportation and long periods of storage, the concentration of the anti-VEGF antibody being at least about 50 mg/ml, 60 mg/ml, 80 mg/ml, 90 mg/ml, 100 mg/ml, 120 mg/ml, 140 mg/ml, 160 mg/ml, 180 mg/ml, or 200 mg/ml.

The invention provides aqueous pharmaceutical compositions comprising an anti-VEGF antibody, a stabilizer, a buffer, and a surfactant. In certain aspects, as aqueous pharmaceutical composition comprises: (i) at least 50 mg/ml of an anti-VEGF antibody, (ii) a sugar (such as sucrose) as a stabilizer, (iii) a citrate or histidine buffer, and (iv) polysorbate 80 as a surfactant.

In certain aspects, the aqueous pharmaceutical composition comprises at least 50 mg/ml of an anti-VEGF antibody comprising the sequences of SEQ ID NO: 1 and SEQ ID NO: 2, about 4.5% to 11% (w/v) sucrose, 10-20 mM citrate buffer, and 0.001% to 0.05% polysorbate 80 (w/v), wherein the pH of the composition is about 7.0 to about 7.6.

Specific preferred embodiments of the invention will become evident from the following more detailed description of certain preferred embodiments and the claims.

BRIEF DESCRIPTION OF THE DRAWINGS

FIG. 1: Antibody 1008 in formulations 1 to 6 (F1 to F6) with PEG at 5% after 165 days.

DETAILED DESCRIPTION OF THE INVENTION

The invention provides aqueous pharmaceutical compositions comprising a high concentration of an anti-VEGF antibody. In certain embodiments an aqueous pharmaceutical composition of the invention is stable for at least 18 months at 2-8° C. and is suitable for administration to the eye, including injection or infusion, e.g., ophthalmic administration, e.g., intravitreal administration.

The present invention provides novel pharmaceutical formulations, in particular novel pharmaceutical formulations in which the active ingredient comprises antibodies to human VEGF. In one aspect, the invention relates to an aqueous pharmaceutical composition with high concentration of anti-VEGF antibodies. Preferred anti-VEGF antibodies in formulations of the invention are described in WO 2009/155724, the entire contents of which are hereby incorporated by reference.

The term "antibody" as used herein includes whole antibodies and any antigen binding fragment (i.e., "antigen-binding portion," "antigen binding polypeptide," or "immunobinder") or single chain thereof. An "antibody" includes a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion") refers to one or more fragments of an antibody that retain the ability to specifically bind to an antigen (e.g., VEGF). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a single domain or dAb fragment (Ward et al., (1989) Nature 341: 544-546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins. Antibodies can be of different isotype, for example, an IgG (e.g., an IgG1, IgG2, IgG3, or IgG4 subtype), IgA1, IgA2, IgD, IgE, or IgM antibody.

In a preferred embodiment, an aqueous pharmaceutical composition of the invention comprises a variable heavy chain having the sequence as set forth in SEQ ID NO: 1 and a variable light chain having the sequence as set forth in SEQ ID NO: 2.

VH:

SEQ ID NO: 1
EVQLVESGGGLVQPGGSLRLSCTASGFSLTDYYYMTWVRQAPGKGLEWV

GFIDPDDDPYYATWAKGRFTISRDNSKNTLYLQMNSLRAEDTAVYYCAG

GDHNSGWGLDIWGQGTLVTVSS

VL:

SEQ ID NO: 2
EIVMTQSPSTLSASVGDRVIITCQASEIIHSWLAWYQQKPGKAPKLLIY

LASTLASGVPSRFSGSGSGAEFTLTISSLQPDDFATYYCQNVYLASTNG

ANFGQGTKLTVLG

In another preferred embodiment, the anti-VEGF antibody is a single-chain Fv (scFv) antibody fragment comprising the sequence as set forth in SEQ ID NO: 3:

(SEQ ID NO: 3)
EIVMTQSPSTLSASVGDRVIITCQASEIIHSTNLATNYQQKPGKAPKLLI

YLASTLASGVPSRFSGSGSGAEFTLTISSLQPDDFATYYCQNVYLASTNG

ANFGQGTKLTVLGGGGSGGGGSGGGGSGGGGSEVQLVESGGGLVQPGGS

LRLSCTASGFSLTDYYYMTTNVRQAPGKGLETNVGFIDPDDDPYYATTNA

```
KGRFTISRDNSKNTLYLQMNSLRAEDTAVYYCAGGDHNSGTNGLDITNGQ

GTLVTVSS
```

An anti-VEGF antibody in an aqueous pharmaceutical composition of the invention can be produced, for example, as described in WO 2009/155724. An scFv can be produced using an expression vector, as described therein. A methionine derived from the start codon in an expression vector is present in the final protein in cases where it has not been cleaved posttranslationally:

```
                                         (SEQ ID NO: 4)
MEIVMTQSPS TLSASVGDRV IITCQASEII HSWLAWYQQK

PGKAPKLLIY LASTLASGVP SRFSGSGSGA EFTLTISSLQ

PDDFATYYCQ NVYLASTNGA NFGQGTKLTV LGGGGGSGGG

GSGGGGSGGG GSEVQLVESG GGLVQPGGSL RLSCTASGFS

LTDYYYMTWV RQAPGKGLEW VGFIDPDDDP YYATWAKGRF

TISRDNSKNT LYLQMNSLRA EDTAVYYCAG GDHNSGWGLD

IWGQGTLVTV SS
```

In certain embodiments, the anti-VEGF antibody in an aqueous pharmaceutical composition of the invention comprises heavy chain HCDR1, HCDR2 and HCDR 3 as set forth in SEQ ID NO: 5, 6, and 7, respectively, and light chain LCDR1, LCDR2 and LCDR3 as set forth in SEQ ID NO: 8, 9, and 10, respectively.

| CDR | SEQ ID | Sequence |
| --- | --- | --- |
| HCDR1 | SEQ ID NO: 5 | GFSLTDYYYMT |
| HCDR2 | SEQ ID NO: 6 | FIDPDDDPYYATWAKG |
| HCDR3 | SEQ ID NO: 7 | GDHNSGWGLDI |
| LCDR1 | SEQ ID NO: 8 | QASEIIHSWLA |
| LCDR2 | SEQ ID NO: 9 | LASTLAS |
| LCDR3 | SEQ ID NO: 10 | QNVYLASTNGAN |

In one embodiment, the concentration of an anti-VEGF antibody in the aqueous pharmaceutical composition of the invention is at least 50 mg/ml. Preferably, the aqueous pharmaceutical composition of the invention comprises about 50 mg/ml, about 60 mg/ml, about 70 mg/ml, about 80 mg/ml, about 90 mg/ml, about 100 mg/ml, about 110 mg/ml, about 120 mg/ml, about 130 mg/ml, about 140 mg/ml, about 150 mg/ml, about 160 mg/ml, about 170 mg/ml, about 180 mg/ml, about 190 mg/ml, about 200 mg/ml, about 210 mg/ml, about 220 mg/ml, about 230 mg/ml, about 240 mg/ml, about 250 mg/ml or about 300 mg/ml of an anti-VEGF antibody.

In certain embodiments, the aqueous pharmaceutical composition of the invention comprises between about 60 mg/ml and about 120 mg/ml of an anti-VEGF antibody, for example, an antibody comprising SEQ ID NO: 1 and SEQ ID NO: 2.

In one embodiment, the aqueous pharmaceutical composition of the invention comprises between about 60 mg/ml and about 120 mg/ml of an anti-VEGF antibody, comprising SEQ ID NO: 3.

In one embodiment, the aqueous pharmaceutical composition of the invention comprises about 60 mg/ml of an anti-VEGF antibody comprising SEQ ID NO: 3.

In one embodiment, the aqueous pharmaceutical composition of the invention comprises about 90 mg/ml of an anti-VEGF antibody comprising SEQ ID NO: 3.

In another embodiment, the aqueous pharmaceutical composition of the invention comprises about 120 mg/ml of an anti-VEGF antibody comprising SEQ ID NO: 3.

In one embodiment, the aqueous pharmaceutical composition of the invention comprises between about 60 mg/ml and about 120 mg/ml of an anti-VEGF antibody, comprising SEQ ID NO: 4.

In one embodiment, the aqueous pharmaceutical composition of the invention comprises about 60 mg/ml of an anti-VEGF antibody comprising SEQ ID NO: 4.

In another embodiment, the aqueous pharmaceutical composition of the invention comprises about 120 mg/ml of an anti-VEGF antibody comprising SEQ ID NO: 4.

As used herein, the term "about" includes and describes the value or parameter per se. For example, "about x" includes and describes "x" per se. As used herein, the term "about" when used in association with a measurement, or used to modify a value, a unit, a constant, or a range of values, refers to variations of ±1-10% in addition to including the value or parameter per se. In some embodiments, the term "about" when used in association with a measurement, or used to modify a value, a unit, a constant, or a range of values, refers to variations of ±1, ±2, ±3, ±4, ±5, ±6, ±7, ±8, ±9, or ±10%.

As used herein, the term "between" includes and describes the value or parameter per se. For example, "between x and y" includes and describes "x" and "y".

As used herein, the term "stable" means that the anti-VEGF antibody as described herein essentially retains its physical stability and/or chemical stability and/or biological activity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993), for example. Stability can be measured at a selected temperature for a selected time period, for example using AEX-HPLC (Anion exchange high performance liquid chromatography) as described herein. Preferably, the aqueous formulation is stable at room temperature (about 25° C.) or at 40° C. for at least 1 week and/or stable at about 2-8° C. for at least 3 months, at least 12 months, at least 18 months, or at least 24 months.

The anti-VEGF antibody as described herein "retains its physical stability" in a pharmaceutical formulation if it meets the defined release specifications for aggregation, degradation, precipitation and/or denaturation upon visual examination of color and/or clarity, or as measured by UV light scattering, AEX-HPLC, or by size exclusion chromatography (SEC), or other suitable methods known in the art.

In particular, it retains its physical stability if it meets the requirements for ophthalmic solutions stipulated in U.S. Pharmacopeial Convention General Chapter <789>. In one embodiment, an aqueous pharmaceutical composition of the invention meets the USP <789> requirements relative to the presence of particulate matter. Thus, in certain embodiments, the maximum number of particles ≥10 μm diameter in an aqueous pharmaceutical composition of the invention is 50 per mL, the maximum number of particles ≥25 μm diameter in an aqueous pharmaceutical composition of the invention is 5 per mL, and the maximum number of particles ≥50 μm diameter in an aqueous pharmaceutical composition of the invention is 2 per mL, said particle numbers being determined by the light obscuration and/or microscopic particle count method as required by the U.S. Pharmacopeial Convention General Chapter <789>).

As used herein, the term "protein aggregation" means the formation of protein species of higher molecular weight, such as oligomers or multimers, instead of the desired defined species of the biopharmaceutical drug (e.g., a monomer). Protein aggregation is thus a universal term for the formation of all kinds of not further defined multimeric species that are formed by covalent bonds or noncovalent interactions. Aggregates can be measured by Size Exclusion Chromatography (SE-HPLC or SEC). In one embodiment, aggregates of the anti-VEGF antibody in the aqueous pharmaceutical formulation are below the limit of quantitation.

The anti-VEGF antibody as described herein "retains its stability" in an aqueous pharmaceutical formulation, if the purity of the antibody does not decrease, or does not substantially decrease, after storage at room temperature (about 25° C.) or at 40° C. for at least 1 week and/or stable at about 2-8° C. for at least 3 months to 18 months. Stability of the anti-VEGF antibody may be assessed by any suitable means, for example, size-exclusion chromatography (SEC), capillary gel electrophoresis and/or anion exchange chromatography (AEX). In one embodiment, the anti-VEGF antibody is stable in an aqueous pharmaceutical composition, wherein the % loss in main peak assessed by SEC is ≤5%, ≤4%, ≤3%, ≤2%, ≤1%, ≤0.5%, ≤0.4%, ≤0.3%, ≤0.2% or ≤0.1% assessed after storage at room temperature (about 25° C.) or at 40° C. for at least 1 week and/or at about 2-8° C. for at least 3 months, at least 6 months, at least 9 months, at least 12 months, or at least 18 months. In a preferred embodiment, the anti-VEGF antibody has ≤0.5%, ≤0.4%, ≤0.3%, ≤0.2% or ≤0.1% loss in main peak assessed by SEC after storage at about 2-8° C. for at least 3 months, at least 6 months, at least 9 months, at least 12 months, or at least 18 months. In a particularly preferred embodiment, the anti-VEGF antibody has ≤0.1% loss in main peak assessed by SEC after storage at about 2-8° C. for at least 3 months, at least 6 months, at least 9 months, at least 12 months, or at least 18 months.

In one embodiment, the anti-VEGF antibody is stable in an aqueous pharmaceutical composition, wherein the % loss in sum of HC and LC assessed by capillary gel electrophoresis, for example under reducing conditions, e.g., SDS, is ≤5%, ≤4%, ≤3%, ≤2%, ≤1%, ≤0.5%, ≤0.4%, ≤0.3%, or ≤0.2% assessed after storage at room temperature (about 25° C.) or at 40° C. for at least 1 week and/or at about 2-8° C. for at least 3 months, at least 6 months, at least 9 months, at least 12 months, or at least 18 months. In a preferred embodiment, the anti-VEGF antibody has ≤0.5%, ≤0.4%, ≤0.3%, or ≤0.2% loss in sum of HC and LC assessed by capillary gel electrophoresis after storage at about 2-8° C. for at least 3 months, at least 6 months, at least 9 months, at least 12 months, or at least 18 months. In a particularly preferred embodiment, the anti-VEGF antibody has ≤0.2% loss in sum of HC and LC assessed by capillary gel electrophoresis after storage at about 2-8° C. for at least 3 months, at least 6 months, at least 9 months, at least 12 months, or at least 18 months.

In one embodiment, the anti-VEGF antibody is stable in an aqueous pharmaceutical composition, wherein the % sum of acidic peaks assessed by anion exchange chromatography (AEX) is ≤2%, ≤1.9%, ≤1.8%, ≤1.7%, or ≤1.6% assessed after storage at about 2-8° C. for at least 3 months, at least 6 months, at least 9 months, at least 12 months, or at least 18 months. In a preferred embodiment, the anti-VEGF antibody has ≤2% sum of acidic peaks assessed by anion exchange chromatography after storage at about 2-8° C. for at least 3 months, at least 6 months, at least 9 months, at least 12 months, or at least 18 months. In another embodiment, the anti-VEGF antibody is stable in an aqueous pharmaceutical composition, wherein the % sum of acidic peaks assessed by anion exchange chromatography (AEX) is ≤6%, ≤5%, or ≤4% assessed after storage at about 25° C. for at least 3 months, at least 6 months, at least 9 months, at least 12 months, or at least 18 months.

In one embodiment, the anti-VEGF antibody is stable in an aqueous pharmaceutical composition, wherein the % sum of basic peaks assessed by anion exchange chromatography (AEX) is ≤2%, ≤1.9%, or ≤1.8% assessed after storage at about 2-8° C. for at least 3 months, at least 6 months, at least 9 months, at least 12 months, or at least 18 months. In a preferred embodiment, the anti-VEGF antibody has ≤2% sum of basic peaks assessed by anion exchange chromatography after storage at about 2-8° C. for at least 3 months, at least 6 months, at least 9 months, at least 12 months, or at least 18 months. In another embodiment, the anti-VEGF antibody is stable in an aqueous pharmaceutical composition, wherein the % sum of basic peaks assessed by anion exchange chromatography (AEX) is ≤6%, ≤5%, or ≤4% assessed after storage at about 25° C. for at least 3 months, at least 6 months, at least 9 months, at least 12 months, or at least 18 months.

The anti-VEGF antibody as described herein "retains its biological activity" in an aqueous pharmaceutical formulation, if the biological activity of the antibody at a given time is within about 10% of the biological activity exhibited at the time the pharmaceutical formulation was prepared as determined in a potency assay, for example in a HUVEC proliferation potency assay. An example of a potency analysis is a competition ELISA. For example in a competitive ELISA, the ability of 1008, as described in the Examples herein, to compete with VEGFR2/Fc for biotinylated VEGF can be measured. The signal observed is inversely related to the concentration of 1008, as increasing amounts of 1008 effectively block the binding of biotinylated VEGF with its receptor VEGFR2/Fc. Each sample can be analyzed in a 96-well microtiter plate against a 1008 reference standard, and the relative potency of the sample to that of the reference standard can be observed.

In one embodiment, the anti-VEGF antibody is stable in an aqueous pharmaceutical composition, wherein the biological activity of the anti-VEGF antibody is between about 65% and 135% compared to a reference sample and wherein biological activity is assessed after storage at about 2-8° C. for at least 3 months, at least 6 months, at least 9 months, at least 12 months, or at least 18 months.

As used herein, an "aqueous" pharmaceutical composition is a composition suitable for pharmaceutical use, wherein the aqueous carrier is distilled water. A composition suitable for pharmaceutical use may be sterile, homogeneous and/or isotonic. Aqueous pharmaceutical compositions may be prepared either directly in an aqueous form, for example in pre-filled syringe ready for use or in a syringe prepared from a vial the comprises a pharmaceutical composition of the invention (the "liquid formulations") or as lyophilisate to be reconstituted shortly before use. As used herein, the term "aqueous pharmaceutical composition" refers to the liquid formulation or reconstituted lyophilized formulation. In certain embodiments, the aqueous pharmaceutical compositions of the invention are suitable for ophthalmic administration to a human subject. In a specific embodiment, the aqueous pharmaceutical compositions of the invention are suitable for intravitreal administration.

The aqueous pharmaceutical compositions of the invention comprises, in addition to the anti-VEGF antibody, further components such as one or more of the following: (i) a stabilizer; (ii) a buffering agent; (iii) a surfactant; and (iv) a free amino acid. Inclusion of each of such additional components can give compositions with low aggregation of the anti-VEGF antibody. Preferably, the aqueous pharmaceutical compositions of the invention include, in addition to the anti-VEGF antibody: (i) a stabilizer; (ii) a buffering agent; and (iii) a surfactant.

Suitable stabilizer for use with the invention can act, for example, as viscosity enhancing agents, bulking agents, solubilizing agents, and/or the like. The stabilizer can be ionic or non-ionic (e.g. sugars). As sugars they include, but are not limited to, monosaccharides, e.g., fructose, maltose, galactose, glucose, D-mannose, sorbose and the like; disaccharides, e.g. lactose, sucrose, trehalose, cellobiose, and the like; polysaccharides, e.g. raffinose, melezitose, maltodextrins, dextrans, starches, and the like; and alditols, such as mannitol, xylitol, maltitol, lactitol, xylitol sorbitol (glucitol) and the like. For example, the sugar may be sucrose, trehalose, raffinose, maltose, sorbitol or mannitol. The sugar may be a sugar alcohol or an amino sugar, such as sucrose or trehalose. Sucrose is preferred. As ionic stabilizer they may include salts such as NaCl or amino acid components such as arginine-HCl. In a preferred embodiment, a sugar is present in the aqueous pharmaceutical composition of the invention, at a concentration of between 3 and 11% (w/v). In certain embodiments, the sugar is sucrose at a concentration of about 4.5% to about 11%. In other embodiments, the sugar is sucrose at a concentration of about 5.5% to about 7.0% (w/v) sucrose. In other embodiments, the sugar is sucrose at a concentration of about 5.5% to about 6.8% (w/v) sucrose. In other embodiments, the sugar is trehalose at a concentration of about 5% to about 10%. In a preferred embodiment, the aqueous pharmaceutical composition comprises a concentration of 5.8% (w/v) sucrose. In another preferred embodiment, the aqueous pharmaceutical composition comprises a concentration of 6.4% (w/v) sucrose.

Suitable buffering agents for use with the invention include, but are not limited to, organic acid salts such as salts of citric acid, ascorbic acid, gluconic acid, carbonic acid, tartaric acid, succinic acid, acetic acid or phthalic acid; Tris, tromethamine hydrochloride, or phosphate buffer. In addition, amino acid components can also be used as buffering agent. Citrate or histidine buffer are particularly useful, including 10-20 mM of histidine buffer, for example, 0.13% to 0.26% (w/v) histidine and 0.03%-0.07% (w/v) histidine Hydrochloride monohydrate), or 10-20 mM citrate buffer, for example 0.006% to 0.012% citric acid (w/v) and 0.2% to 0.6% sodium citrate (w/v). Citric acid used in a formulation of the invention can be any hydration form, for example anhydrous or monohydrate. In a preferred embodiment, the aqueous pharmaceutical composition comprises a buffering agent at a concentration of between about 1 and 60 mM, e.g., about 10-40 mM, about 15-30 mM, about 15-25 mM, about 10-20 mM, about 10-15 mM. In certain embodiments, the buffering agent is citrate or histidine. In a preferred embodiment, the aqueous pharmaceutical composition comprises about 10-15 mM sodium citrate, for example about 0.01 mg/mL citric acid monohydrate and about 0.43 mg/mL sodium citrate dihydrate The aqueous pharmaceutical compositions include such buffering agent or pH adjusting agent to provide improved pH control. In certain embodiment, an aqueous pharmaceutical composition of the invention has a pH between 7.0 and 7.6. In one embodiment, the pH of an aqueous pharmaceutical composition of the invention is about 7.0-7.5, or about 7.0-7.4, about 7.0-7.3, about 7.0-7.2, about 7.1-7.6, about 7.2-7.6, about 7.3-7.6 or about 7.4-7.6. In one embodiment, an aqueous pharmaceutical composition of the invention has a pH of about 7.0, about 7.1, about 7.2, about 7.3, about 7.4, about 7.5 or about 7.6. In a preferred embodiment, the aqueous pharmaceutical composition has a pH of ≥7.0 In a preferred embodiment, the aqueous pharmaceutical composition has a pH of about 7.2. In another preferred embodiment, the aqueous pharmaceutical composition has a pH of about 7.4. In another preferred embodiment, the aqueous pharmaceutical composition has a pH of about 7.6.

As used herein, the term "surfactant" herein refers to organic substances having amphipathic structures. Surfactants can be classified, depending on the charge of the surface-active moiety, into nonionic, anionic, cationic and dispersing agents for various pharmaceutical compositions and preparations of biological materials.

Suitable surfactants for use with the invention include, but are not limited to, non-ionic surfactants, ionic surfactants and zwitterionic surfactants. Typical surfactants for use with the invention include, but are not limited to, sorbitan fatty acid esters (e.g., sorbitan monocaprylate, sorbitan monolaurate, sorbitan monopalmitate), sorbitan trioleate, glycerine fatty acid esters (e.g., glycerine monocaprylate, glycerine monomyristate, glycerine monostearate), polyglycerine fatty acid esters (e.g., decaglyceryl monostearate, decaglyceryl distearate, decaglyceryl monolinoleate), polyoxyethylene sorbitan fatty acid esters (e.g., polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, polyoxyethylene sorbitan tristearate), polyoxyethylene sorbitol fatty acid esters (e.g., polyoxyethylene sorbitol tetrastearate, polyoxyethylene sorbitol tetraoleate), polyoxyethylene glycerine fatty acid esters (e.g., polyoxyethylene glyceryl monostearate), polyethylene glycol fatty acid esters (e.g., polyethylene glycol distearate), polyoxyethylene alkyl ethers (e.g., polyoxyethylene lauryl ether), polyoxyethylene polyoxypropylene alkyl ethers (e.g., polyoxyethylene polyoxypropylene glycol, polyoxyethylene polyoxypropylene propyl ether, polyoxyethylene polyoxypropylene cetyl ether), polyoxyethylene alkylphenyl ethers (e.g., polyoxyethylene nonylphenyl ether), polyoxyethylene hydrogenated castor oils (e.g., polyoxyethylene castor oil, polyoxyethylene hydrogenated castor oil), polyoxyethylene beeswax derivatives (e.g., polyoxyethylene sorbitol beeswax), polyoxyethylene lanolin derivatives (e.g., polyoxyethylene lanolin), and polyoxyethylene fatty acid amides (e.g., polyoxyethylene stearic acid amide); $C_{10}$-$C_{18}$ alkyl sulfates (e.g. sodium cetyl sulfate, sodium lauryl sulfate, sodium oleyl sulfate), polyoxyethylene $C_{10}$-$C_{18}$ alkyl ether sulfate with an average of 2 to 4 moles of ethylene oxide units added (e.g., sodium polyoxyethylene lauryl sulfate), and $C_1$-$C_{18}$ alkyl sulfosuccinate ester salts (e.g., sodium lauryl sulfosuccinate ester); and natural surfactants such as lecithin, glycerophospholipid, sphingophospholipids (e.g., sphingomyelin), and sucrose esters of $C_{12-18}$ fatty acids. A composition may include one or more of these surfactants. Preferred surfactants are polyoxyethylene sorbitan fatty acid esters e.g. polysorbate 20, 40, 60 or 80. Polysorbate 80 is particularly preferred. In one embodiment, the aqueous pharmaceutical composition comprises 0.001% to 0.05% polysorbate 80 (w/v). In another embodiment, the aqueous pharmaceutical composition comprises 0.001% to 0.01% polysorbate 80

(w/v). In yet another embodiment, the aqueous pharmaceutical composition comprises 0.001% to 0.005% polysorbate 80 (w/v). In a preferred embodiment, the aqueous pharmaceutical composition comprises 0.001%, 0.002%, 0.003%, 0.004% or 0.005% polysorbate 80 (w/v). In one embodiment, the aqueous pharmaceutical composition comprises 0.001% polysorbate 80 (w/v). In one embodiment, the aqueous pharmaceutical composition comprises 0.002% polysorbate 80 (w/v). In one embodiment, the aqueous pharmaceutical composition comprises 0.003% polysorbate 80 (w/v). In one embodiment, the aqueous pharmaceutical composition comprises 0.004% polysorbate 80 (w/v). In one embodiment, the aqueous pharmaceutical composition comprises 0.005% polysorbate 80 (w/v). In another preferred embodiment, the aqueous pharmaceutical composition comprises 0.01% to 0.05% polysorbate 80 (w/v). In one embodiment, the aqueous pharmaceutical composition comprises 0.01% polysorbate 80 (w/v). In one embodiment, the aqueous pharmaceutical composition comprises 0.02% polysorbate 80 (w/v). In one embodiment, the aqueous pharmaceutical composition comprises 0.03% polysorbate 80 (w/v). In one embodiment, the aqueous pharmaceutical composition comprises 0.04% polysorbate 80 (w/v). In one embodiment, the aqueous pharmaceutical composition comprises 0.05% polysorbate 80 (w/v).

Suitable free amino acids for use with the invention include, but are not limited to, arginine, lysine, histidine, ornithine, isoleucine, leucine, alanine, glycine, glutamic acid or aspartic acid. The inclusion of a basic amino acid is preferred i.e. arginine, lysine and/or histidine. If a composition includes histidine then this may act both as a buffering agent and a free amino acid, but when a histidine buffer is used it is typical to include a non-histidine free amino acid e.g. to include histidine buffer and lysine. An amino acid may be present in its D- and/or L-form, but the L-form is typical. The amino acid may be present as any suitable salt e.g., a hydrochloride salt, such as arginine-HCl. In one preferred embodiment, an aqueous pharmaceutical composition of the invention does not comprise any such free amino acids.

Other contemplated excipients, which may be utilized in the aqueous pharmaceutical compositions of the invention include, for example, antimicrobial agents, antioxidants, antistatic agents, lipids such as phospholipids or fatty acids, steroids such as cholesterol, protein excipients such as serum albumin (human serum albumin), recombinant human albumin, gelatin, casein, salt-forming counterions such sodium and the like. These and additional known pharmaceutical excipients and/or additives suitable for use in the formulations of the invention are known in the art, e.g., as listed in "The Handbook of Pharmaceutical Excipients, 4th edition, Rowe et al., Eds., American Pharmaceuticals Association (2003); and Remington: the Science and Practice of Pharmacy, 21$^{st}$ edition, Gennaro, Ed., Lippincott Williams & Wilkins (2005). In one embodiment, the aqueous pharmaceutical composition comprises NaCl. In one embodiment, the aqueous pharmaceutical composition comprises 120 mM NaCl. In one embodiment, the aqueous pharmaceutical composition comprises hyaluronic acid (HA). Hyaluronic acid includes, but is not limited to, HA with a molecular weight of 500-700 kDa. In one embodiment, the aqueous pharmaceutical composition comprises 0.1% HA. In another embodiment, the aqueous pharmaceutical composition comprises 0.2% HA.

In certain embodiments, lyophilisation of an anti-VEGF antibody is contemplated to provide an aqueous pharmaceutical composition of the invention for treating a patient. Techniques for lyophilisation of antibodies are well known in the art e.g. see John F. Carpenter and Michael J. Pikal, 1997 (*Pharm. Res.* 14, 969-975); Xialin (Charlie) Tang and Michael J. Pikal, 2004 (*Pharm. Res.* 21, 191-200). Accordingly, in one embodiment provided is a lyophilized formulation prepared by lyophilizing the aqueous pharmaceutical composition described herein. In another embodiment, provided is a method for preparing a lyophilisate, comprising the steps of: (i) preparing an aqueous pharmaceutical composition comprising an anti-VEGF antibody as described herein and (ii) lyophilizing the aqueous solution.

Before a lyophilisate can be administered to a patient it should be reconstituted with an aqueous reconstituent. This step permits antibody and other components in the lyophilisate to re-dissolve to give a solution which is suitable for injection to a patient.

The volume of aqueous material used for reconstitution dictates the concentration of the antibody in a resulting pharmaceutical composition. Reconstitution with a smaller volume of reconstituent than the pre-lyophilisation volume provides a composition which is more concentrated than before lyophilisation. The reconstitution factor (volume of formulation after lyophilization:volume of formulation before lyophilization) may be from 1:0.5 to 1:6. A reconstitution factor of 1:3 is useful. As mentioned above, lyophilisates of the invention can be reconstituted to give aqueous compositions with an anti-VEGF antibody concentration of at least 50 mg/ml (i.e., at least 60, 70, 80, 90, 100, 110, 120, or 130 mg/ml), and the volume of reconstituent will be selected accordingly. If required, the reconstituted formulation can be diluted prior to administration to a patient as appropriate to deliver the intended dose.

Typical reconstituents for lyophilized antibodies include sterile water or buffer, optionally containing a preservative. If the lyophilisate includes a buffering agent then the reconstituent may include further buffering agent (which may be the same as or different from the lyophilisate's buffering agent) or it may instead include no buffering agent (e.g. WFI (water for injection), or physiological saline).

The aqueous pharmaceutical composition described herein may be in the form of a liquid. In a preferred embodiment, the aqueous pharmaceutical composition is in the form of a liquid. In one embodiment, the aqueous pharmaceutical composition is comprised as a liquid in a vial.

The aqueous pharmaceutical compositions of the invention comprising anti-VEGF antibodies can be used to treat a variety of diseases or disorders. Pharmaceutical compositions comprising anti-VEGF antibodies are particularly useful to treat neovascular ocular diseases in a subject.

A "neovascular ocular disease" that can be treated using an aqueous pharmaceutical composition of the invention includes, a condition, disease, or disorder associated with ocular neovascularization, including, but not limited to, abnormal angiogenesis, choroidal neovascularization (CNV), retinal vascular permeability, retinal edema, diabetic retinopathy (particularly proliferative diabetic retinopathy), diabetic macular edema, neovascular (exudative) age-related macular degeneration (AMD), including CNV associated with nAMD (neovascular AMD), sequela associated with retinal ischemia, Central Retinal Vein Occlusion (CRVO), and posterior segment neovascularization.

The aqueous pharmaceutical compositions of the invention may include further active ingredients in addition to the anti-VEGF antibody. Further pharmacological agents may include, for instance, other antibodies useful for treating ocular diseases.

The terms "treat," "treating," and "treatment," as used herein refer to therapeutic measures described herein. The methods of "treatment" employ administration to a subject, in need of such treatment, an antibody of the present invention, for example, a subject having a VEGF-mediated ocular disorder or a subject who ultimately may acquire such a disorder, in order to prevent, cure, delay, reduce the severity of, or ameliorate one or more symptoms of the disorder or recurring disorder, or in order to prolong the survival of a subject beyond that expected in the absence of such treatment.

Aqueous pharmaceutical compositions of the invention can be administered to a patient. As used herein, the term "subject" or "patient" refers to human and non-human mammals, including but, not limited to, primates, rabbits, pigs, horses, dogs, cats, sheep, and cows. Preferably, a subject or patient is a human.

Administration will typically be via a syringe. Thus the invention provides a delivery device (e.g., a syringe) including a pharmaceutical composition of the invention (e.g., pre-filled syringe), and a kit comprising a syringe and a vial that includes a pharmaceutical composition of the invention. Patients will receive an effective amount of the anti-VEGF antibody as the principal active ingredient (i.e., an amount that is sufficient to achieve or at least partially achieve the desired effect). A therapeutically effective dose is sufficient if it can produce even an incremental change in the symptoms or conditions associated with the disease. The therapeutically effective dose does not have to completely cure the disease or completely eliminate symptoms. Preferably, the therapeutically effective dose can at least partially arrest the disease and its complications in a patient already suffering from the disease. Amounts effective for this use will depend upon the severity of the disorder being treated and the general state of the patient's own immune system.

The dose amount can be readily determined using known dosage adjustment techniques by a physician having ordinary skill in treatment of the disease or condition. The therapeutically effective amount of an anti-VEGF antibody used in an aqueous pharmaceutical composition of the invention is determined by taking into account the desired dose volumes and mode(s) of administration, for example. Typically, therapeutically effective compositions are administered in a dosage ranging from 0.001 mg/ml to about 200 mg/ml per dose. Preferably, a dosage used in a method of the invention is about 60 mg/ml to about 120 mg/ml (i.e., about 60, 70, 80, 90, 100, 110, or 120 mg/ml). In a preferred embodiment, the dosage of an anti-VEGF antibody used in a method of the invention is 60 mg/ml or 120 mg/ml.

In certain embodiments, a dose is administered directly to an eye of a patient. In one embodiment, a dose per eye is at least about 0.5 mg up to about 6 mg. Preferred doses per eye include about 0.5 mg, 0.6 mg, 0.7 mg, 0.8 mg, 0.9 mg, 1.0 mg, 1.2 mg, 1.4 mg, 1.6 mg, 1.8 mg, 2.0 mg, 2.5 mg, 3.0 mg, 3.5 mg, 4.0 mg, 4.5 mg, 5.0 mg, 5.5 mg, and 6.0 mg. Doses can be administered in various volumes suitable for ophthalmic administration, such as 50 µl or 100 µl, for example, including 3 mg/50 µl or 6 mg/50 µl. Smaller volumes can also be used, including 20 µl or less, for example about 20 µl, about 10 µl, or about 8.0 µl. In certain embodiments, a dose of 2.4 mg/20 µl, 1.2 mg/10 µl or 1 mg/8.0 µl (e.g., 1 mg/8.3 µl) is delivered to an eye of a patient for treating or ameliorating one or more of the diseases and disorders described above. Delivery can be, for example, by intravitreal injection or infusion.

The invention also provides formulations (i.e., aqueous pharmaceutical compositions) of the invention for use as medicaments, e.g., for use in delivering an antibody to a patient, or for use in treating or ameliorating one or more of the diseases and disorders described above.

The invention further provides a method for delivering an anti-VEGF antibody to a patient, comprising a step of administering to the patient an aqueous pharmaceutical composition of the invention.

In certain embodiments, a method for delivering an anti-VEGF antibody to a patient invention comprises the steps of: (i) reconstituting a lyophilisate of the invention to give an aqueous formulation, and (ii) administering the aqueous formulation to the patient. Step (ii) ideally takes place within 24 hours of step (i) (e.g., within 12 hours, within 6 hours, within 3 hours, or within 1 hour).

In one embodiment, the aqueous pharmaceutical composition is comprised in a vial. In another embodiment, the aqueous pharmaceutical composition is comprised in a delivery device. In one embodiment, such delivery device is a pre-filled syringe. In one embodiment a method for delivering an anti-VEGF antibody to a patient comprises administering the aqueous pharmaceutical composition by intravitreal injection.

Certain specific embodiments of the invention are described as numbered hereafter:

1. An aqueous pharmaceutical composition comprising at least 50 mg/ml to about 120 mg/ml of an anti-VEGF antibody comprising the sequences of SEQ ID NO: 1 and SEQ ID NO: 2, about 4.5% to 11% (w/v) sucrose, 5-20 mM sodium citrate, and 0.001% to 0.05% polysorbate 80 (w/v), wherein the pH of the composition is about 7.0 to about 7.6.
2. The aqueous pharmaceutical composition according to embodiment 1, wherein the anti-VEGF antibody comprises the sequence of SEQ ID NO: 3.
3. The aqueous pharmaceutical composition according to embodiment 1 or 2, wherein the anti-VEGF antibody comprises the sequence of SEQ ID NO: 4.
4. The aqueous pharmaceutical composition of any of the preceding embodiments, wherein the pH of the composition is about 7.0.
5. The aqueous pharmaceutical composition of any of the preceding embodiments, wherein the pH of the composition is about 7.1.
6. The aqueous pharmaceutical composition of any of the preceding embodiments, wherein the pH of the composition is about 7.2.
7. The aqueous pharmaceutical composition of any of the preceding embodiments, wherein the pH of the composition is about 7.3.
8. The aqueous pharmaceutical composition of any of the preceding embodiments, wherein the pH of the composition is about 7.4.
9. The aqueous pharmaceutical composition of any of the preceding embodiments, comprising 0.004% polysorbate 80 (w/v).
10. The aqueous pharmaceutical composition of any of the preceding embodiments, comprising 0.02% polysorbate 80 (w/v).
11. The aqueous pharmaceutical composition of any of the preceding embodiments, comprising between about 60 mg/ml and about 120 mg/ml of an anti-VEGF antibody.
12. The aqueous pharmaceutical composition of any of the preceding embodiments, comprising about 60 mg/ml of an anti-VEGF antibody.

13. The aqueous pharmaceutical composition of any of the preceding embodiments, comprising about 120 mg/ml of an anti-VEGF antibody
14. The aqueous pharmaceutical composition of any of the preceding embodiments, comprising 5.5% to 7.0% (w/v) sucrose.
15. The aqueous pharmaceutical composition of any of the preceding embodiments, comprising 10-12 mM citrate buffer.
16. The aqueous pharmaceutical composition of any of the preceding embodiments, comprising 5.9% (w/v) sucrose, 10 mM sodium citrate, 0.02% (w/v) polysorbate 80, and wherein the pH is about 7.2.
17. The aqueous pharmaceutical composition of embodiment 16, comprising 6 mg of an anti-VEGF antibody.
18. The aqueous pharmaceutical composition of any of the preceding embodiments, comprising 6.4% (w/v) sucrose, 12 mM sodium citrate, 0.02% (w/v) polysorbate 80, and wherein the pH is about 7.2.
19. The aqueous pharmaceutical composition of any of the preceding embodiments, comprising 5.8% (w/v) sucrose, 10 mM sodium citrate, 0.02% (w/v) polysorbate 80, and wherein the pH is about 7.2.
20. The aqueous pharmaceutical composition of embodiment 18 or 19, comprising 3 mg of an anti-VEGF antibody.
21. The aqueous pharmaceutical composition of any of the preceding embodiments, further comprising NaCl.
22. The aqueous pharmaceutical composition of any of the preceding embodiments, further comprising 0.1-0.5% hyaluronic acid (HA).
23. The aqueous pharmaceutical composition of any of the preceding embodiments, wherein said composition is stable for at least 18 months at 2-8° C.
24. The aqueous pharmaceutical composition of any of the preceding embodiments, wherein said composition is liquid.
25. A method for delivering an anti-VEGF antibody to a subject, comprising administering to said subject the aqueous pharmaceutical composition of any of embodiments 1-24.
26. A method of treating an ocular disease or disorder that is mediated by VEGF, comprising administering to a subject the aqueous pharmaceutical composition of any of embodiments 1-24.
27. The method of embodiment 26, wherein said ocular disease or disorder is an ocular neovascular disease.
28. The method of any of embodiments 24-27, wherein said administration is intravitreally.
29. An aqueous pharmaceutical composition of any one of embodiments 1-24 for use in delivering an anti-VEGF antibody to a subject, comprising a step of administering the aqueous pharmaceutical composition to the subject.
30. An aqueous pharmaceutical composition of any one of embodiments 1-24 for use in treating an ocular disease or disorder that is mediated by VEGF, comprising administering the aqueous pharmaceutical composition to a subject.
31. An aqueous pharmaceutical composition for use according to embodiment 30, wherein said ocular disease or disorder is an ocular neovascular disease.
32. An aqueous pharmaceutical composition for use according to any of embodiments 29-31, wherein said administration is intravitreally.
33. A dosage form comprising the aqueous pharmaceutical composition of any of the embodiments 1-24.
34. A delivery device comprising the aqueous pharmaceutical composition of any of embodiments 1-24.
35. The delivery device of embodiment 34, which is a pre-filled syringe.

The skilled person realizes that the features, aspects and embodiments taught in the text are all combinable with each other and particular aspects combining features and/or embodiments from various parts of the text will be considered to be adequately disclosed to the skilled person.

It is to be understood that each embodiment may be combined with one or more other embodiments, to the extent that such a combination is consistent with the description of the embodiments. It is further to be understood that the embodiments provided above are understood to include all embodiments, including such embodiments as result from combinations of embodiments.

As used herein, all percentages are percentages by weight, unless stated otherwise.

As used herein and unless otherwise indicated, the terms "a" and "an" are taken to mean "one", "at least one" or "one or more". Unless otherwise required by context, singular terms used herein shall include pluralities and plural terms shall include the singular.

As used herein, the term "comprising" encompasses "including" as well as "consisting" and "essentially consisting of", e.g., a composition comprising X may consist exclusively of X or may include something additional, e.g., X+Y.

The term "or" is used herein to mean, and is used interchangeably with the term "and/or", unless context clearly indicates otherwise.

The contents of any patents, patent applications, and references cited throughout this specification are hereby incorporated by reference in their entireties.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

EXAMPLES

The following examples describe formulation development efforts designed to identify suitable stabilization approaches and compositions to provide stable, highly concentrated solutions comprising the antibody 1008, enabling an intravitreal (IVT) formulation with at least an 12-month shelf-life at refrigerated storage conditions that meets the regulatory requirements for ophthalmic products.

The 1008 antibody is a single-chain antibody that binds to and inhibits the biologic activity of human vascular endothelial growth factor A (VEGF-A). The amino acid sequence of expressed 1008 is SEQ ID NO: 4.

Sub-visible particulates were observed at a concentration of 120 mg/ml 1008 when 1008 was formulated as an isotonic solution in 15 mM trisodium citrate/citric acid with 0.05% polysorbate 80 at pH 6.75. The major issue with this initial formulation was the particulate matter exceeding regulatory limits for ophthalmic solutions for injection (USP<789>).

The following examples summarize the formulation development of 60 and 120 mg/ml 1008 intravitreal (IVT) solutions stable at 2-8° C. storage for at least 18 months. The formulation development effort focused on inhibition of the formation of sub-visible particles and meeting the USP requirement for content, purity and potency.

Analytical Methods

The following methods were used throughout the Examples as indicated.

Micro-Flow Imaging (MFI) Method

MFI method used for analysis of excipient screening, Study 1 and Study 2 for 60 mg/ml optimization studies was as follows:

Total sample volume used: 0.50 mL
Purge volume: 0.20 mL
Analysis volume: 0.26 mL The optimize illumination step was performed with purified filtered particle free water. MFI method used for analysis of 120 mg/ml 1008 Study 3 and Study 4:

Total sample volume used: 0.80 mL
Purge volume: 0.23 mL
Analysis volume: 0.48 mL The optimize illumination step was performed with purified filtered particle free water.

SEC Method

SE-HPLC (Size exclusion chromatography) separates proteins according to their size. Separation was achieved by the differential exclusion, or inclusion, of the sample molecules as they passed through the porous-particle stationary phase. High performance liquid chromatography system capable of maintaining a flow rate of 0.25 ml/minute and a sample temperature of 4° C., equipped with a TOSOH SuperSW3000 column (Tosoh Bioscience LLC, King of Prussia, PA), and a detector capable of operating at 214 nm and 280 nm simultaneously. This method was used for purity testing.

AEX-HPLC Method

AEX-HPLC (Anion exchange high performance liquid chromatography) separates proteins according to their net charge. This procedure was performed using high-performance liquid chromatography (HPLC), capable of maintaining a flow rate of 0.8 ml/minute, with a temperature controlled column compartment (set at 25° C.) containing a strong anion exchange column, an auto-sampler (set at 4° C.), and a variable wavelength UV detector, capable of operating at 280 nm.

CGE Method

The capillary gel electrophoresis method was performed for the determination of the identity and purity of proteins between the molecular weights of 10 kDa and 225 kDa by SDS gel Capillary Electrophoresis. The capillary was dynamically filled with a Beckman Coulter 0.2% SDS Gel Buffer, pH 8, proprietary formulation. The separation of the protein was performed by molecular sieving electrophoresis. The logarithm of protein molecular weight was linear with its reciprocal electrophoretic mobility. The identity of a protein was determined by comparing its migration with a molecular weight standard. The purity was determined by area percent analysis of the parent peak and impurities. A photodiode array detector (PDA) was used to analyze the sample at 220 nm.

Example 1

Formulation Screening Study with 6 Formulations

A formulation screening study was performed to identify a suitable formulation to address the issue of crystal/cloudiness/turbidity formation observed upon storage of 1008 at a concentration of 120 mg/mL.

Five formulations (F2-F6) with varying amounts of salt (0 and 120 mM NaCl), polysorbate 80 (PS80) (0.05% and 0.004%), and pH values (6.8, 7.0, 7.3 and 7.6) were tested and compared to control (F1). Table 1 provides details on the composition on formulation F1 to F6.

TABLE 1

Formulation screening

| Formulation | Antibody 1008 | pH | Sucrose | Citrate buffer | Polysorbate 80 | NaCl |
|---|---|---|---|---|---|---|
| Formulation 1 (F1) | 120 mg/mL | 6.8 | 5.9% | 10 mM | 0.05% | 0 |
| Formulation 2 (F2) | 120 mg/mL | 6.8 | 5.9% | 10 mM | 0.004% | 120 mM |
| Formulation 3 (F3) | 120 mg/mL | 7.0 | 5.9% | 10 mM | 0.004% | 0 |
| Formulation 4 (F4) | 120 mg/mL | 7.3 | 5.9% | 10 mM | 0.004% | 0 |
| Formulation 5 (F5) | 120 mg/mL | 7.3 | 5.9% | 10 mM | 0.05% | 0 |
| Formulation 6 (F6) | 120 mg/mL | 7.6 | 5.9% | 10 mM | 0.004% | 0 |

Turbidity and pH

In formulation 2 an increase in turbidity was observed with a 120 mM NaCl concentration at pH 6.8 after 4 weeks at 40° C. In the results were correlated with pH to show the pH effect. Formulations 4 and 5 were formulated at pH 7.3 with low and high polysorbate 80 concentrations. Turbidity values for these two formulations (F4 and F5) were within one digit from each other at all time points and conditions (Table 2), and these values were not considered significantly different. A pH effect was seen with the data, where higher pH values corresponded to lower turbidity. Slightly higher turbidity was also observed at 5° C. and 25° C. with F2 comprising NaCl as compared to the formulations without NaCl. For all six formulations, the target pH was stable upon storage at 5° C. and 25° C. for up to 12 months. All the pH values were within the acceptable range of target pH.

Sub-Visible Particle by Light Obscuration

Particle counts for all formulations up to 52 weeks at 5° C. and 25° C. were within the USP<789> limits. The measurements were performed using a non-USP small volume light obscuration method. No difference between the formulations was observed.

Purity/Main Peak by SEC

Purity as assessed by size exclusion chromatography (SEC) was stable over 12 months at 5° C., with no significant decrease observed for any formulations. A significant decrease in main peak purity by SEC was observed at 25° C. with increasing pH and increasing polysorbate 80. Overall the model showed that for main peak by SEC, polysorbate 80 had a more significant effect than pH. The formulations which maximize main peak purity by SEC at 25° C. were those containing low polysorbate 80 concentrations and at pH values of 6.8 and 7.0. The decrease in main peak was due primarily to formation of aggregates by SEC.

Purity/Main Peak by AEX

Purity as assessed by anion exchange chromatography (AEX) decreased over 12 months stability at 5° C. (approx. 1% decrease in AEX purity over 12 months at 5° C.). At accelerated and stressed stability conditions a significant decrease in AEX purity was observed (approx. 12% decrease in AEX purity over 6 months at 25° C.). Changes in AEX main peak appeared mainly temperature and time driven. No relevant differences were observed between pH set points. The effect of NaCl was observed at 5° C. and 25° C. by AEX for the F2 formulation (pH 6.8, 0.004% PS80, 120 mM NaCl), suggesting that NaCl had a stabilizing effect and minimized the decrease in AEX purity due to temperature stress. Purity by AEX decreased approx. 27% up to 6 weeks at 40° C. Higher polysorbate 80 concentration (0.05%) resulted in significant decrease in main peak purity as compared to formulations with lower polysorbate 80 concentration (0.004%). Combined purity data (SEC and AEX) for all six formulations at 40° C. (4 weeks) showed a decrease in purity with increasing pH and increasing polysorbate 80 concentration.

Purity/Main Peak by CE-SDS

Purity of antibody 1008 as assessed by capillary-electrophoresis sodium dodecyl sulfate (CE-SDS) under reducing conditions decreased over 12 months at 5° C. by approximately 0.7%. Under accelerated condition at 25° C. up to 6 months purity of antibody 1008 as assessed by CE-SDS under reducing conditions decreased by approx. 5%, and confirmed that the level of fragmentation increased with increasing pH but showed no impact with respect to polysorbate 80 concentration.

Overall, the stability results for pH, ionic strength, and polysorbate 80 concentration confirmed that pH and polysorbate 80 concentration were the most significant factors at all temperatures. Formulations with higher pH and higher polysorbate 80 resulted in lower purity by SEC and AEX. The addition of salt had a minimal impact on stability with no relevant impact on sub-visible particulates. All analytical results up to 12 months (52 weeks) of the formulation stability study are summarized in Table 2.

TABLE 2

Analytical results of formulation screening stability

| Time-point | Formulation | Turbidity NTU | PS 80 % (w/w) | pH | Light obscuration (#/mL) >10 μm | >25 μm | >50 μm | Total particle counts | CE-SDS (reducing) Purity (sum of LC and HC [%]) |
|---|---|---|---|---|---|---|---|---|---|
| T = 0 | F1 | 6.6 | 0.067 | 6.83 | 27 | 0 | 0 | 761 | 99.5 |
|  | F2 | 8.06 | 0.003 | 6.83 | 10 | 0 | 0 | 238 | 99.5 |
|  | F3 | 5.99 | 0.003 | 6.97 | 10 | 2 | 0 | 262 | 99.5 |
|  | F4 | 5.34 | 0.004 | 7.27 | 9 | 0 | 0 | 203 | 99.6 |
|  | F5 | 5.48 | 0.069 | 7.3 | 18 | 0 | 0 | 296 | 99.6 |
|  | F6 | 5.7 | 0.005 | 7.57 | 0 | 0 | 0 | 115 | 99.5 |
| T = 2 W (40° C.) | F1 | 7.32 | n.t | 6.8 | 40 | 1 | 0 | 475 | 98.2 |
|  | F2 | 10.8 | n.t | 6.78 | 51 | 7 | 0 | 1534 | 98.2 |
|  | F3 | 6.69 | n.t | 6.96 | 30 | 0 | 0 | 509 | 97.9 |
|  | F4 | 6.14 | n.t | 7.29 | 14 | 7 | 0 | 338 | 97.4 |
|  | F5 | 6.28 | n.t | 7.26 | 39 | 6 | 0 | 241 | 97.5 |
|  | F6 | 5.9 | n.t | 7.53 | 7 | 0 | 0 | 323 | 96.9 |
| T = 4 W (40° C.) | F1 | 10.7 | n.t | 6.83 | 5 | 2 | 0 | 510 | 97.1 |
|  | F2 | 23.3 | n.t | 6.8 | 20 | 0 | 0 | 812 | 97.2 |
|  | F3 | 9.95 | n.t | 6.98 | 1 | 0 | 0 | 480 | 96.8 |
|  | F4 | 8.45 | n.t | 7.27 | 9 | 0 | 0 | 737 | 96 |
|  | F5 | 8.93 | n.t | 7.29 | 0 | 0 | 0 | 160 | 96.1 |
|  | F6 | 10.2 | n.t | 7.59 | 8 | 1 | 0 | 308 | 95.2 |
| T = 6 W (5° C.) | F1 | 6.32 | n.t | 6.75 | 10 | 1 | 0 | 477 | 99.6 |
|  | F2 | 8.41 | n.t | 6.74 | 21 | 1 | 0 | 789 | 99.7 |
|  | F3 | 6.18 | n.t | 6.93 | 15 | 1 | 0 | 341 | 99.5 |
|  | F4 | 5.13 | n.t | 7.23 | 4 | 1 | 0 | 130 | 99.6 |
|  | F5 | 6.23 | n.t | 7.23 | 9 | 0 | 0 | 273 | 99.6 |
|  | F6 | 5.71 | n.t | 7.47 | 20 | 1 | 0 | 319 | 99.6 |
| T = 6 W (25° C.) | F1 | 6.85 | n.t | 6.76 | 1 | 0 | 0 | 306 | 98.8 |
|  | F2 | 8.15 | n.t | 6.75 | 15 | 1 | 0 | 650 | 98.8 |
|  | F3 | 6.26 | n.t | 6.93 | 24 | 1 | 0 | 607 | 98.7 |
|  | F4 | 5.65 | n.t | 7.24 | 19 | 3 | 0 | 414 | 98.4 |
|  | F5 | 5.72 | n.t | 7.29 | 12 | 1 | 0 | 476 | 98.5 |
|  | F6 | 5.08 | n.t | 7.56 | 19 | 3 | 0 | 396 | 98 |
| T = 3 M (5° C.) | F1 | 6.22 | n.t | 6.8 | 22 | 3 | 0 | 449 | n.t |
|  | F2 | 7.89 | n.t | 6.82 | 7 | 0 | 0 | 181 | n.t |
|  | F3 | 6.19 | n.t | 6.98 | 9 | 0 | 0 | 205 | n.t |
|  | F4 | 5.6 | n.t | 7.34 | 6 | 0 | 0 | 224 | n.t |
|  | F5 | 5.15 | n.t | 7.29 | 10 | 0 | 0 | 490 | n.t |
|  | F6 | 5.39 | n.t | 7.54 | 16 | 0 | 0 | 288 | n.t |
| T = 3 M (25° C.) | F1 | 6.39 | n.t | 6.8 | 10 | 0 | 0 | 541 | n.t |
|  | F2 | 8.19 | n.t | 6.78 | 16 | 0 | 0 | 1076 | n.t |
|  | F3 | 5.92 | n.t | 6.96 | 7 | 0 | 0 | 508 | n.t |
|  | F4 | 5.43 | n.t | 7.28 | 6 | 0 | 0 | 393 | n.t |
|  | F5 | 5.92 | n.t | 7.3 | 11 | 0 | 0 | 310 | n.t |
|  | F6 | 5.59 | n.t | 7.57 | 29 | 0 | 0 | 835 | n.t |
| T = 6 M (5° C.) | F1 | 6.09 | 0.069 | 6.8 | 0 | 0 | 0 | 327 | 99.1 |
|  | F2 | 8.29 | 0.004 | 6.75 | 1 | 0 | 0 | 461 | 99.1 |
|  | F3 | 6.15 | 0.004 | 6.94 | 0 | 0 | 0 | 34 | 98.9 |
|  | F4 | 5.88 | 0.006 | 7.25 | 0 | 0 | 0 | 28 | 98.8 |
|  | F5 | 5.84 | 0.069 | 7.28 | 1 | 1 | 0 | 74 | 98.8 |
|  | F6 | 5.25 | 0.005 | 7.55 | 2 | 2 | 0 | 250 | 98.5 |
| T = 6 M (25° C.) | F1 | 6.71 | 0.067 | 6.81 | 4 | 0 | 0 | 352 | 96.3 |
|  | F2 | 8.03 | 0.002 | 6.78 | 0 | 0 | 0 | 203 | 95.9 |
|  | F3 | 5.98 | 0.005 | 6.98 | 1 | 1 | 0 | 164 | 95.4 |
|  | F4 | 5.37 | 0.004 | 7.3 | 0 | 0 | 0 | 272 | 93.9 |

TABLE 2-continued

| | | | | | | | | | |
|---|---|---|---|---|---|---|---|---|---|
| | F5 | 5.33 | 0.071 | 7.28 | 3 | 0 | 0 | 229 | 93.7 |
| | F6 | 5.12 | 0.004 | 7.56 | 0 | 0 | 0 | 280 | 92.6 |
| T = 9 M | F1 | 7.75 | n.t | 6.77 | 0 | 0 | 0 | 248 | n.t |
| (5° C.) | F2 | 8.67 | n.t | 6.74 | 6 | 0 | 0 | 268 | n.t |
| | F3 | 6.58 | n.t | 6.93 | 0 | 0 | 0 | 1395 | n.t |
| | F4 | 6.51 | n.t | 7.24 | 4 | 0 | 0 | 86 | n.t |
| | F5 | 6.49 | n.t | 7.24 | 0 | 0 | 0 | 117 | n.t |
| | F6 | 6.28 | n.t | 7.5 | 0 | 0 | 0 | 9 | n.t |
| T = 12 M | F1 | 6.67 | 0.062 | 6.79 | 1 | 0 | 0 | 178 | 99 |
| (5° C.) | F2 | 7.94 | 0.003 | 6.74 | 1 | 0 | 0 | 60 | 98.9 |
| | F3 | 6.31 | 0.004 | 6.94 | 4 | 0 | 0 | 67 | 98.9 |
| | F4 | 5.65 | 0.004 | 7.28 | 1 | 0 | 0 | 51 | 98.7 |
| | F5 | 5.54 | 0.063 | 7.29 | 1 | 0 | 0 | 51 | 98.7 |
| | F6 | 5.63 | 0.004 | 7.54 | 3 | 0 | 0 | 39 | 98.4 |

| Time-point | Formu-lation | Turbidity NTU | PS 80 % (w/w) | pH | AEX [%] AEX sum basic peaks | AEX main peak | AEX sum acidic peaks | Relative area at RRT 1.5 | Relative area at RRT 1.53 | SEC SEC main peak % |
|---|---|---|---|---|---|---|---|---|---|---|
| T = 0 | F1 | 6.6 | 0.067 | 6.83 | 0.7 | 97.95 | 1.34 | 0 | 0 | 100 |
| | F2 | 8.06 | 0.003 | 6.83 | 0.7 | 97.88 | 1.42 | 0 | 0 | 100 |
| | F3 | 5.99 | 0.003 | 6.97 | 0.68 | 97.99 | 1.33 | 0 | 0 | 100 |
| | F4 | 5.34 | 0.004 | 7.27 | 0.65 | 97.96 | 1.39 | 0 | 0 | 100 |
| | F5 | 5.48 | 0.069 | 7.3 | 0.6 | 98.11 | 1.29 | 0 | 0 | 100 |
| | F6 | 5.7 | 0.005 | 7.57 | 0.62 | 98.04 | 1.34 | 0 | 0 | 100 |
| T = 2 W (40° C.) | F1 | 7.32 | n.t | 6.8 | 5.67 | 83.19 | 11.14 | 1.05 | 6.74 | 90.3 |
| | F2 | 10.8 | n.t | 6.78 | 5.09 | 87.14 | 7.77 | 0.49 | 1.25 | 94.5 |
| | F3 | 6.69 | n.t | 6.96 | 5.45 | 86.44 | 8.11 | 0.56 | 1.19 | 94 |
| | F4 | 6.14 | n.t | 7.29 | 4.08 | 86.77 | 9.16 | 0.46 | 1.33 | 93.1 |
| | F5 | 6.28 | n.t | 7.26 | 3.81 | 83.08 | 13.1 | 0.65 | 3.12 | 88.4 |
| | F6 | 5.9 | n.t | 7.53 | 3.53 | 86.23 | 10.24 | 0.6 | 1.6 | 92.1 |
| T = 4 W (40° C.) | F1 | 10.7 | n.t | 6.83 | 6.94 | 66.27 | 26.8 | 2.39 | 7.56 | 74.4 |
| | F2 | 23.3 | n.t | 6.8 | 6.3 | 74.41 | 19.29 | 1.57 | 4.11 | 84.2 |
| | F3 | 9.95 | n.t | 6.98 | 6.84 | 73.65 | 19.51 | 0 | 15.71 | 83.2 |
| | F4 | 8.45 | n.t | 7.27 | 5.18 | 73.36 | 21.46 | 0 | 17.61 | 81 |
| | F5 | 8.93 | n.t | 7.29 | 4.55 | 64.74 | 30.71 | 0 | 27.14 | 70.2 |
| | F6 | 10.2 | n.t | 7.59 | 4.32 | 71.75 | 23.93 | 0 | 19.93 | 78.7 |
| T = 6 W (5° C.) | F1 | 6.32 | n.t | 6.75 | 1.14 | 97.36 | 1.5 | 0 | 0 | 100 |
| | F2 | 8.41 | n.t | 6.74 | 1.03 | 97.48 | 1.47 | 0 | 0 | 100 |
| | F3 | 6.18 | n.t | 6.93 | 1.09 | 97.39 | 1.52 | 0 | 0 | 100 |
| | F4 | 5.13 | n.t | 7.23 | 1.06 | 97.43 | 1.52 | 0 | 0 | 100 |
| | F5 | 6.23 | n.t | 7.23 | 0.98 | 97.54 | 1.47 | 0 | 0.02 | 99.9 |
| | F6 | 5.71 | n.t | 7.47 | 1.06 | 97.43 | 1.51 | 0 | 0.01 | 100 |
| T = 6 W (25° C.) | F1 | 6.85 | n.t | 6.76 | 3.52 | 94.29 | 2.19 | 0.07 | 0.01 | 99.6 |
| | F2 | 8.15 | n.t | 6.75 | 2.94 | 94.96 | 2.19 | 0.04 | 0.01 | 99.8 |
| | F3 | 6.26 | n.t | 6.93 | 3.14 | 94.8 | 2.06 | 0.05 | 0.01 | 99.8 |
| | F4 | 5.65 | n.t | 7.24 | 2.75 | 94.97 | 2.27 | 0.08 | 0.01 | 99.7 |
| | F5 | 5.72 | n.t | 7.29 | 2.7 | 94.91 | 2.39 | 0.11 | 0.03 | 99.5 |
| | F6 | 5.08 | n.t | 7.56 | 2.74 | 94.65 | 2.61 | 0.11 | 0.03 | 99.6 |
| T = 3 M (5° C.) | F1 | 6.22 | n.t | 6.8 | 1.1 | 97.33 | 1.57 | 0 | 0 | 99.9 |
| | F2 | 7.89 | n.t | 6.82 | 1.05 | 97.37 | 1.58 | 0 | 0 | 99.9 |
| | F3 | 6.19 | n.t | 6.98 | 1.07 | 97.34 | 1.58 | 0 | 0 | 99.8 |
| | F4 | 5.6 | n.t | 7.34 | 1.02 | 97.37 | 1.61 | 0 | 0 | 99.9 |
| | F5 | 5.15 | n.t | 7.29 | 0.99 | 97.37 | 1.64 | 0 | 0.02 | 99.9 |
| | F6 | 5.39 | n.t | 7.54 | 1.03 | 97.27 | 1.69 | 0 | 0.01 | 99.9 |
| T = 3 M (25° C.) | F1 | 6.39 | n.t | 6.8 | 5.29 | 91.4 | 3.31 | 0.17 | 0.12 | 99.1 |
| | F2 | 8.19 | n.t | 6.78 | 4.31 | 92.55 | 3.13 | 0.1 | 0.09 | 99.4 |
| | F3 | 5.92 | n.t | 6.96 | 4.71 | 92.19 | 3.09 | 0.12 | 0.09 | 99.4 |
| | F4 | 5.43 | n.t | 7.28 | 3.95 | 92.61 | 3.44 | 0.2 | 0.1 | 99.3 |
| | F5 | 5.92 | n.t | 7.3 | 3.81 | 92.31 | 3.88 | 0.3 | 0.13 | 98.8 |
| | F6 | 5.59 | n.t | 7.57 | 3.69 | 92.37 | 3.94 | 0.28 | 0.1 | 99 |
| T = 6 M (5° C.) | F1 | 6.09 | 0.069 | 6.8 | 1.59 | 96.62 | 1.78 | 0 | 0 | 99.9 |
| | F2 | 8.29 | 0.004 | 6.75 | 1.38 | 96.83 | 1.79 | 0 | 0 | 99.9 |
| | F3 | 6.15 | 0.004 | 6.94 | 1.45 | 96.76 | 1.79 | 0 | 0 | 100 |
| | F4 | 5.88 | 0.006 | 7.25 | 1.37 | 96.77 | 1.85 | 0 | 0 | 99.9 |
| | F5 | 5.84 | 0.069 | 7.28 | 1.29 | 96.89 | 1.81 | 0 | 0 | 99.9 |
| | F6 | 5.25 | 0.005 | 7.55 | 1.41 | 96.64 | 1.95 | 0 | 0 | 99.9 |
| T = 6 M (25° C.) | F1 | 6.71 | 0.067 | 6.81 | 8.62 | 83.68 | 7.7 | 0.1 | 0.15 | 95.9 |
| | F2 | 8.03 | 0.002 | 6.78 | 7.22 | 86.25 | 6.53 | 0.07 | 0.1 | 97.7 |
| | F3 | 5.98 | 0.005 | 6.98 | 7.82 | 85.49 | 6.69 | 0.08 | 0.14 | 97.5 |
| | F4 | 5.37 | 0.004 | 7.3 | 6.34 | 86.09 | 7.56 | 0.14 | 0.23 | 96.8 |
| | F5 | 5.33 | 0.071 | 7.28 | 5.99 | 84.8 | 9.2 | 0.21 | 0.24 | 94.8 |
| | F6 | 5.12 | 0.004 | 7.56 | 6.02 | 85 | 8.98 | 0.15 | 0.26 | 95.8 |
| T = 9 M (5° C.) | F1 | 7.75 | n.t | 6.77 | 1.75 | 96.3 | 1.62 | 0 | 0.01 | 99.9 |
| | F2 | 8.67 | n.t | 6.74 | 1.48 | 96.6 | 1.63 | 0 | 0.01 | 99.9 |
| | F3 | 6.58 | n.t | 6.93 | 1.6 | 96.5 | 1.6 | 0 | 0.01 | 99.9 |
| | F4 | 6.51 | n.t | 7.24 | 1.41 | 96.5 | 1.71 | 0 | 0.01 | 99.9 |

TABLE 2-continued

|   |    | F5 | 6.49 | n.t   | 7.24 | 1.38 | 96.5  | 1.72 | 0.01 | 0.02 | 99.8 |
|---|----|----|------|-------|------|------|-------|------|------|------|------|
|   |    | F6 | 6.28 | n.t   | 7.5  | 1.54 | 96.3  | 1.86 | 0.01 | 0.02 | 99.8 |
| T = 12 |    | F1 | 6.67 | 0.062 | 6.79 | 1.78 | 96.2  | 1.58 | 0.02 | 0    | 99.8 |
| M |    | F2 | 7.94 | 0.003 | 6.74 | 1.57 | 96.5  | 1.59 | 0.01 | 0    | 99.9 |
| (5° C.) |    | F3 | 6.31 | 0.004 | 6.94 | 1.68 | 96.43 | 1.57 | 0.01 | 0    | 99.9 |
|   |    | F4 | 5.65 | 0.004 | 7.28 | 1.53 | 96.41 | 1.71 | 0.02 | 0.01 | 99.9 |
|   |    | F5 | 5.54 | 0.063 | 7.29 | 1.37 | 96.39 | 1.7  | 0.04 | 0.02 | 99.8 |
|   |    | F6 | 5.63 | 0.004 | 7.54 | 1.59 | 96.06 | 1.87 | 0.02 | 0.02 | 99.8 |

PEG Model Assay

A PEG model was developed to enable rapid selection of suitable formulations for antibody 1008 at 120 mg/mL. First, a suitable PEG concentration was defined at which antibody 1008 in the original formulation at pH 6.8 would form visible crystals after approximately 7 days storage at 2-8° C. PEG concentrations of 1, 2, 4, 5, 6 and 8% were prepared.

TABLE 3

PEG assay—concentration selection

| Sample ID No. | Antibody 1008 | pH | Sucrose | Citrate | Polysorbate 80 | PEG 20 kDa |
|---|---|---|---|---|---|---|
| 1 | 120 mg/ml | 6.75 | 5.9% | 10 mM | 0.004% | 1% |
| 2 | 120 mg/ml | 6.75 | 5.9% | 10 mM | 0.004% | 2% |
| 3 | 120 mg/ml | 6.75 | 5.9% | 10 mM | 0.004% | 4% |
| 5 | 120 mg/ml | 6.75 | 5.9% | 10 mM | 0.004% | 5% |

TABLE 3-continued

PEG assay—concentration selection

| Sample ID No. | Antibody 1008 | pH | Sucrose | Citrate | Polysorbate 80 | PEG 20 kDa |
|---|---|---|---|---|---|---|
| 6 | 120 mg/ml | 6.75 | 5.9% | 10 mM | 0.004% | 6% |
| 4 | 120 mg/ml | 6.75 | 5.9% | 10 mM | 0.004% | 8% |

PEG pellets were added directly to antibody 1008 and dissolved for about 10 minutes by magnetic stirring. Five vials containing 1 mL each were prepared for each PEG concentration and the vials were stored at two temperature conditions—temperature (2-8° C., with cycling and at 40° C. stable). Daily visual observations were made on each vial for 1 week. All vials with the 8% PEG formulation displayed a solid crystalline formation after 48 hours, which then was observed to separate into two phases. For the PEG 6% vials, crystallization began at day three in 3 vials and all 5 vials formed a solid white crystals after six days. For the 5% PEG samples, all vials began to crystallize at day six. For the PEG 4% vials, crystallization started at day eight in 4 of 5 vials and the 5th vial crystallized after 30 days. The PEG 1% and 2% vials all remained clear after 30 days. Based on these results, the 5% PEG concentration was chosen for further screening studies.

Five vials containing 1 mL each were prepared for formulations 1 to 6 as described in Table 1 daily visual observation on each vial. Study design and test conditions are described in Table 4 and the results after 165 days (5.5 months) are shown in FIGURE. All vials of F1 (control, pH 6.8) were precipitated after 7 days. Precipitation started after 19 days for F2 (120 mM NaCl, pH 6.8) vials and after 22 days for the F3 vials (pH 7.0). All vials of the remaining formulations (F4, F5, and F6) were clear after 165 days. Based on this study, crystallization was mitigated three times longer at pH 7.0 vs the control (up to 22 days) and even longer at higher pH (7.3 to 7.6) with all vials of F4, F5, F6 remaining clear after 165 days (5.5 months). Higher pH (>7.0) levels were correlated with the avoidance of crystallization. The presence of NaCl was also correlated with avoidance of crystallization but for a shorter time period.

TABLE 4

Formulation screening study with PEG at 5 percent

| Formulation | Antibody 1008 | pH | Sucrose | Citrate [mM] | Polysorbate 80 | NaCl [mM] | PEG (20 kDa) | Start of precipitation |
|---|---|---|---|---|---|---|---|---|
| F1 | 120 mg/ml | 6.8 | 5.9% | 10 | 0.05%  | 0   | 5% | Day 7  |
| F2 | 120 mg/ml | 6.8 | 5.9% | 10 | 0.004% | 120 | 5% | Day 19 |
| F3 | 120 mg/ml | 7.0 | 5.9% | 10 | 0.004% | 0   | 5% | Day 22 |
| F4 | 120 mg/ml | 7.3 | 5.9% | 10 | 0.004% | 0   | 5% | none   |
| F5 | 120 mg/ml | 7.3 | 5.9% | 10 | 0.05%  | 0   | 5% | none   |
| F6 | 120 mg/ml | 7.6 | 5.9% | 10 | 0.004% | 0   | 5% | none   |

Robustness Study

A robustness study of antibody 1008 at 120 mg/mL was designed to confirm the selected pH and polysorbate 80 concentration. A target pH of 7.2 with a minimum pH of 7.0 was selected to minimize chemical degradation, aggregation, and the risk of crystal formation and allow a minimal pH range of ±0.2 during manufacturing and long term storage. A target polysorbate 80 concentration of 0.02% was chosen to minimize aggregation and allow a sufficient amount of polysorbate 80 to minimize adsorption and maintain homogeneity. Ten formulations were selected with formulation 1 (F1) as a control with varying amounts of polysorbate 80 (0.01, 0.03% and target 0.02%) and pH value (7.0-7.4, target 7.2). In addition, all samples were shaken at 250 rpm for 3 days at room temperature before placing on stability to simulate manufacturing manipulations and realistic transport conditions. The concentration of the components used in the formulation screening is summarized in Table 5. In addition, all formulations further comprised 5.9% sucrose and 10 mM sodium citrate buffer.

TABLE 5

Formulations used in robustness study

| Sample ID | Antibody 1008 | pH | Polysorbate 80 |
|---|---|---|---|
| F1 (control) | 120 mg/ml | 6.8 | 0.05% |
| F2 | 120 mg/ml | 7.0 | 0.01% |
| F3 | 120 mg/ml | 7.0 | 0.02% |
| F4 | 120 mg/ml | 7.0 | 0.03% |
| F5 | 120 mg/ml | 7.2 | 0.01% |
| F6 (target) | 120 mg/ml | 7.2 | 0.02% |
| F7 | 120 mg/ml | 7.2 | 0.03% |
| F8 | 120 mg/ml | 7.4 | 0.01% |
| F9 | 120 mg/ml | 7.4 | 0.02% |
| F10 | 120 mg/ml | 7.4 | 0.03% |

There was no decrease in purity as assessed by SEC and AEX for all polysorbate 80 and pH levels at 25° C. (T=0) after 3 days of shaking stress. An increase in particulate matter counts greater than 10 micron was observed after 3 days of shaking for F1 (control) as well as F5 with lower polysorbate 80 (0.01%) and F9 with higher pH (7.4). This was not visible for F6. Analytical results for the robustness study at 3 days shaking are summarized in Table 6A and 6B below.

TABLE 6A

Analytical results of robustness study for 10 different formulations (T0 and T3 days after shaking)

| Time-point | Formu-lation | UV Vis mg/mL | Turbidity (NTU) | PS 80 % (w/w) | pH | Light obscuration (#/mL) >10 μm | >25 μm | >50 μm | Total particle counts | CE-SDS (reducing) Purity (sum of LC and HC [%]) | SEC [%] SEC main peak |
|---|---|---|---|---|---|---|---|---|---|---|---|
| T = 0 | F1 | 120.1 | 7.83 | 0.06 | 6.85 | 3 | 0 | 0 | 98 | 99.4 | 100 |
| | F2 | 116.1 | 7.04 | 0.01 | 7.01 | 0 | 0 | 0 | 69 | 99.4 | 100 |
| | F3 | 116.1 | 9.03 | 0.02 | 7.04 | 0 | 0 | 0 | 96 | 99.4 | 100 |
| | F4 | 117.2 | 18 | 0.03 | 7.05 | 12 | 1 | 0 | 119 | 99.4 | 100 |
| | F5 | 118.3 | 8.66 | 0.01 | 7.24 | 1 | 0 | 0 | 67 | 99.3 | 100 |
| | F6 | 116 | 9.58 | 0.02 | 7.25 | 3 | 0 | 0 | 55 | 99.4 | 100 |
| | F7 | 115.8 | 11.9 | 0.03 | 7.25 | 3 | 0 | 0 | 71 | 99.3 | 100 |
| | F8 | 117.3 | 11.9 | 0.01 | 7.45 | 0 | 0 | 0 | 64 | 99.3 | 99.9 |
| | F9 | 117.6 | 11.6 | 0.02 | 7.45 | 0 | 0 | 0 | 42 | 99.3 | 99.9 |
| | F10 | 118.6 | 7.26 | 0.04 | n.t | 3 | 0 | 0 | 76 | 99.2 | 99.9 |
| T = 3 d shaking (25° C.) | F1 | 120.4 | 9.59 | 0.06 | 6.81 | 7 | 0 | 0 | 157 | 99.5 | 100 |
| | F2 | 116.8 | 10.1 | 0.01 | 7.01 | 3 | 0 | 0 | 124 | 99.4 | 100 |
| | F3 | 117.8 | 11.5 | 0.02 | 7.02 | 0 | 0 | 0 | 150 | 99.4 | 100 |
| | F4 | 117.3 | 12.4 | 0.03 | 7.03 | 6 | 0 | 0 | 225 | 99.2 | 100 |
| | F5 | 119.3 | 10.6 | 0.01 | 7.21 | 4 | 3 | 0 | 146 | 99.3 | 99.9 |
| | F6 | 115.9 | 12.5 | 0.02 | 7.22 | 1 | 0 | 0 | 146 | 99.2 | 99.9 |
| | F7 | 113.9 | 9.34 | 0.03 | 7.24 | 0 | 0 | 0 | 106 | 99.3 | 99.9 |
| | F8 | 117.4 | 11 | 0.01 | 7.43 | 1 | 0 | 0 | 81 | 99.3 | 99.9 |
| | F9 | 117.5 | 7.79 | 0.02 | 7.44 | 11 | 1 | 0 | 1333 | 99.2 | 99.9 |
| | F10 | 119.3 | 8.17 | 0.04 | 7.42 | 1 | 0 | 0 | 278 | 99.3 | 99.9 |

TABLE 6B

Analytical results of robustness study for 10 different formulations (T0 and T3 days after shaking)

| Time-point | Formu-lation | UV Vis mg/mL | Turbidity (NTU) | PS 80 % (w/w) | pH | AEX [%] AEX sum basic peaks | AEX main peak | AEX sum acidic peaks | Relative area at RRT 1.5 | Relative area at RRT 1.53 |
|---|---|---|---|---|---|---|---|---|---|---|
| T = 0 | F1 | 120.1 | 7.83 | 0.06 | 6.85 | 0.96 | 97.46 | 1.58 | 0 | 0 |
| | F2 | 116.1 | 7.04 | 0.01 | 7.01 | 0.93 | 97.5 | 1.58 | 0 | 0 |
| | F3 | 116.1 | 9.03 | 0.02 | 7.04 | 0.97 | 97.41 | 1.62 | 0 | 0 |
| | F4 | 117.2 | 18 | 0.03 | 7.05 | 0.91 | 97.5 | 1.59 | 0 | 0 |
| | F5 | 118.3 | 8.66 | 0.01 | 7.24 | 0.88 | 97.53 | 1.59 | 0 | 0 |
| | F6 | 116 | 9.58 | 0.02 | 7.25 | 0.92 | 97.46 | 1.62 | 0 | 0 |
| | F7 | 115.8 | 11.9 | 0.03 | 7.25 | 0.91 | 97.5 | 1.59 | 0 | 0 |
| | F8 | 117.3 | 11.9 | 0.01 | 7.45 | 0.89 | 97.49 | 1.63 | 0 | 0 |
| | F9 | 117.6 | 11.6 | 0.02 | 7.45 | 0.91 | 97.44 | 1.64 | 0 | 0 |
| | F10 | 118.6 | 7.26 | 0.04 | n.t | 0.9 | 97.48 | 1.63 | 0 | 0 |
| T = 3 d shaking (25° C.) | F1 | 120.4 | 9.59 | 0.06 | 6.81 | 1.18 | 97.22 | 1.6 | 0 | 0 |
| | F2 | 116.8 | 10.1 | 0.01 | 7.01 | 1.06 | 97.34 | 1.6 | 0 | 0 |
| | F3 | 117.8 | 11.5 | 0.02 | 7.02 | 1.07 | 97.32 | 1.61 | 0 | 0 |

TABLE 6B-continued

Analytical results of robustness study for 10 different formulations (T0 and T3 days after shaking)

| Time-point | Formu-lation | UV Vis mg/mL | Turbidity (NTU) | PS 80 % (w/w) | pH | AEX [%] AEX sum basic peaks | AEX main peak | AEX sum acidic peaks | Relative area at RRT 1.5 | Relative area at RRT 1.53 |
|---|---|---|---|---|---|---|---|---|---|---|
| | F4 | 117.3 | 12.4 | 0.03 | 7.03 | 1.06 | 97.33 | 1.61 | 0 | 0 |
| | F5 | 119.3 | 10.6 | 0.01 | 7.21 | 1.03 | 97.33 | 1.64 | 0 | 0 |
| | F6 | 115.9 | 12.5 | 0.02 | 7.22 | 1.06 | 97.3 | 1.64 | 0 | 0 |
| | F7 | 113.9 | 9.34 | 0.03 | 7.24 | 1.06 | 97.31 | 1.63 | 0 | 0 |
| | F8 | 117.4 | 11 | 0.01 | 7.43 | 1.01 | 97.33 | 1.66 | 0 | 0 |
| | F9 | 117.5 | 7.79 | 0.02 | 7.44 | 1.03 | 97.3 | 1.67 | 0 | 0 |
| | F10 | 119.3 | 8.17 | 0.04 | 7.42 | 1.04 | 97.29 | 1.67 | 0 | 0 |

Up to the 52 weeks stability time points at 5° C. and 25° C., particle counts in the size range >10 µm and >25 µm stayed well below the USP<789> limit of 50 particles/mL and 5 particles/mL, respectively, for all formulations. Turbidity levels of all formulations at 120 mg/mL stored at 2-8° C. range from 5 to 12 NTU on the mean, with one outlier at 18 NTU (F4) at the initial time point (There was no decrease in purity as assessed by SEC and AEX for all polysorbate 80 and pH levels at 25° C. (T=0) after 3 days of shaking stress. An increase in particulate matter counts greater than 10 micron was observed after 3 days of shaking for F1 (control) as well as F5 with lower polysorbate 80 (0.01%) and F9 with higher pH (7.4). This was not visible for F6. Analytical results for the robustness study at 3 days shaking are summarized in Table 6A and 6B below. Table). The turbidity level in the solution decreased slightly from 10.8 to 6.3 NTU after 3 months stability storage. Beyond this timepoint there was no significant change for any of the formulations up to 52 weeks. No relevant change in color and pH value could be observed for any of the formulations. All formulations showed minimal changes with approx. 1.1-1.2% decrease over 52 weeks in terms of main peak purity assessed by AEX and SEC. There were no observable differences, indicating that formulations are robust over 12 months of storage at 2-8° C.

Purity by SEC: No relevant change in level of aggregates was observed with the maximum observed change being 0.1%. Monomer peak was >99% and showed almost no changes over 12 months storage at 2-8° C.

Aggregates by SEC: All formulations were stable at 2-8° C. over 12 months as the aggregate levels assessed by SEC were below the limit of quantitation.

Purity by CE-SDS: A small decrease was observed over 12 months at 5° C. (approx. 1%), which was more pronounced for formulations with higher pH. The concentration in polysorbate 80 is independent to the formation of fragments. Purity data (25° C., 6 months) confirms the level of fragmentation increases with increasing pH. No impact of polysorbate 80 concentration is seen on purity by CE-SDS.

Analytical results for the robustness studies are summarized in Table 7 below.

TABLE 7

Analytical results of robustness study for 10 formulations (T2W, T4W, T5W, T3M, T6M, T9M and T12M)

| Time-point | Formu-lation | Turbidity (NTU) | UV Vis mg/mL | PS 80 % (w/w) | AEX [%] AEX sum basic peaks | AEX main peak | AEX sum acidic peaks | Relative area at RRT 1.5 | Relative area at RRT 1.53 |
|---|---|---|---|---|---|---|---|---|---|
| T = 2 W (40° C.) | F1 | 8.12 | n.t | n.t | 5.38 | 83.26 | 11.36 | 1.16 | 2.39 |
| | F2 | 7.18 | n.t | n.t | 4.65 | 85.31 | 10.05 | 0.95 | 1.69 |
| | F3 | 7.3 | n.t | n.t | 4.54 | 84.31 | 11.15 | 1.04 | 2.18 |
| | F4 | 7.85 | n.t | n.t | 3.1 | 83.85 | 11.73 | 1.08 | 2.44 |
| | F5 | 7.77 | n.t | n.t | 3.97 | 85.07 | 10.97 | 0.96 | 1.86 |
| | F6 | 9.67 | n.t | n.t | 3.87 | 83.86 | 12.27 | 1.04 | 2.43 |
| | F7 | 7.65 | n.t | n.t | 3.8 | 83.52 | 12.68 | 1.05 | 2.67 |
| | F8 | 8.35 | n.t | n.t | 3.43 | 84.53 | 12.04 | 0.97 | 2.17 |
| | F9 | 10 | n.t | n.t | 3.32 | 83.46 | 13.23 | 1.03 | 2.72 |
| | F10 | 9.65 | n.t | n.t | 3.35 | 82.63 | 14.02 | 1.04 | 3.01 |
| T = 4 W (40° C.) | F1 | 11.6 | n.t | n.t | 6.8 | 65.78 | 27.42 | 2.84 | 7.86 |
| | F2 | 9.63 | n.t | n.t | 5.97 | 69.8 | 24.22 | 2.32 | 5.94 |
| | F3 | 9.69 | n.t | n.t | 5.66 | 67.24 | 27.1 | 2.37 | 7.26 |
| | F4 | 10.1 | n.t | n.t | 5.6 | 66.33 | 28.07 | 2.4 | 7.91 |
| | F5 | 8.79 | n.t | n.t | 5.01 | 69.27 | 25.72 | 2.1 | 6.53 |
| | F6 | 9.63 | n.t | n.t | 4.85 | 65.82 | 29.34 | 2.17 | 8.26 |
| | F7 | 9.23 | n.t | n.t | 4.7 | 64.81 | 30.49 | 2.17 | 8.92 |
| | F8 | 8.65 | n.t | n.t | 4.32 | 67.32 | 28.37 | 1.99 | 7.38 |
| | F9 | 9.75 | n.t | n.t | 4.14 | 64.74 | 31.12 | 1.99 | 8.88 |
| | F10 | 9.13 | n.t | n.t | 4.12 | 62.97 | 32.91 | 2.01 | 9.71 |
| T = 5 W (5° C.) | F1 | 9.79 | n.t | 0.06 | 1.19 | 97.14 | 1.67 | 0 | 0.07 |
| | F2 | 7.41 | n.t | 0.01 | 1.14 | 97.18 | 1.69 | 0 | 0.05 |

TABLE 7-continued

|   |   |   |   |   |   |   |   |   |   |
|---|---|---|---|---|---|---|---|---|---|
|   | F3 | 8.17 | n.t | 0.02 | 1.15 | 97.2 | 1.65 | 0 | 0.04 |
|   | F4 | 8.62 | n.t | 0.03 | 1.12 | 97.25 | 1.62 | 0 | 0.02 |
|   | F5 | 8.53 | n.t | 0.01 | 1.07 | 97.29 | 1.63 | 0 | 0.02 |
|   | F6 | 7.67 | n.t | 0.02 | 1.09 | 97.23 | 1.68 | 0 | 0.02 |
|   | F7 | 8 | n.t | 0.04 | 1.08 | 97.29 | 1.63 | 0 | 0.02 |
|   | F8 | 7.88 | n.t | 0.01 | 1.06 | 97.26 | 1.69 | 0 | 0.03 |
|   | F9 | 8.03 | n.t | 0.02 | 1.06 | 97.29 | 1.65 | 0 | 0.03 |
|   | F10 | 8.9 | n.t | 0.04 | 1.06 | 97.28 | 1.66 | 0 | 0.02 |
| T = 5 W | F1 | 10.7 | n.t | 0.05 | 3.22 | 94.23 | 2.53 | 0.08 | 0.04 |
| (25° C.) | F2 | 9.2 | n.t | 0.01 | 3.01 | 94.36 | 2.61 | 0.07 | 0.03 |
|   | F3 | 7.93 | n.t | 0.02 | 2.84 | 94.45 | 2.71 | 0.08 | 0.04 |
|   | F4 | 8.19 | n.t | 0.03 | 2.83 | 94.49 | 2.68 | 0.08 | 0.04 |
|   | F5 | 7.02 | n.t | 0.01 | 2.57 | 94.53 | 2.86 | 0.08 | 0.05 |
|   | F6 | 8.25 | n.t | 0.02 | 2.63 | 94.61 | 2.75 | 0.1 | 0.03 |
|   | F7 | 9.6 | n.t | 0.03 | 2.63 | 94.58 | 2.79 | 0.11 | 0.05 |
|   | F8 | 12.4 | n.t | 0.01 | 2.44 | 94.53 | 3.02 | 0.12 | 0.05 |
|   | F9 | 10.1 | n.t | 0.02 | 2.41 | 94.56 | 3.04 | 0.13 | 0.05 |
|   | F10 | 14.7 | n.t | 0.03 | 2.44 | 94.54 | 3.03 | 0.12 | 0.06 |
| T = 3 M | F1 | 7.15 | 119.1 | 0.0725 | N.A | N.A | N.A | N.A | N.A |
| (5° C.) | F2 | 7.47 | 118.2 | 0.0125 | N.A | N.A | N.A | N.A | N.A |
|   | F3 | 5.99 | 120.4 | 0.0265 | N.A | N.A | N.A | N.A | N.A |
|   | F4 | 5.81 | 120.6 | 0.0405 | N.A | N.A | N.A | N.A | N.A |
|   | F5 | 6.32 | 118.9 | 0.0125 | N.A | N.A | N.A | N.A | N.A |
|   | F6 | 5.97 | 118.2 | 0.0279 | N.A | N.A | N.A | N.A | N.A |
|   | F7 | 5.85 | 118.4 | 0.0396 | N.A | N.A | N.A | N.A | N.A |
|   | F8 | 5.71 | 118.5 | 0.0129 | N.A | N.A | N.A | N.A | N.A |
|   | F9 | 6.12 | 117.2 | 0.0279 | N.A | N.A | N.A | N.A | N.A |
|   | F10 | 6.49 | 120.8 | 0.0418 | N.A | N.A | N.A | N.A | N.A |
| T = 3 M | F1 | 6.57 | 121.5 | 0.0675 | 6.07 | 89.19 | 4.76 | 0.13 | 0.11 |
| (25° C.) | F2 | 6.01 | 121.1 | 0.0122 | 4.89 | 91.04 | 4.07 | 0.15 | 0.16 |
|   | F3 | 5.94 | 120.3 | 0.0268 | 5.26 | 89.85 | 4.88 | 0.21 | 0.08 |
|   | F4 | 6.35 | 119.1 | 0.0406 | 5.28 | 89.75 | 4.97 | 0.23 | 0.1 |
|   | F5 | 6.06 | 119.7 | 0.0123 | 4.38 | 91.04 | 4.58 | 0.2 | 0.17 |
|   | F6 | 5.7 | 118.3 | 0.0268 | 4.8 | 90.1 | 5.1 | 0.26 | 0.08 |
|   | F7 | 6.31 | 120.4 | 0.0404 | 4.76 | 89.67 | 5.57 | 0.3 | 0.09 |
|   | F8 | 5.41 | 120.5 | 0.0122 | 4.47 | 89.81 | 5.71 | 0.3 | 0.09 |
|   | F9 | 5.37 | 121.5 | 0.026 | 4.27 | 90.04 | 5.69 | 0.35 | 0.1 |
|   | F10 | 5.5 | 122.4 | 0.0406 | 4.34 | 90.16 | 5.5 | 0.37 | 0.1 |
| T = 6 M | F1 | 5.86 | n.t | 0.0679 | 1.61 | 96.41 | 1.65 | 0.013 | 0.018 |
| (5° C.) | F2 | 6.01 | n.t | 0.0125 | 1.35 | 96.56 | 1.66 | 0.008 | 0.02 |
|   | F3 | 6.04 | n.t | 0.0258 | 1.35 | 96.58 | 1.68 | 0.017 | 0.012 |
|   | F4 | 6.23 | n.t | 0.0383 | 1.31 | 96.55 | 1.69 | 0.019 | 0.016 |
|   | F5 | 5.88 | n.t | 0.0127 | 1.25 | 96.6 | 1.72 | 0.019 | 0.015 |
|   | F6 | 5.9 | n.t | 0.0291 | 1.33 | 96.54 | 1.75 | 0.017 | 0.022 |
|   | F7 | 5.85 | n.t | 0.0413 | 1.35 | 96.52 | 1.74 | 0.015 | 0.019 |
|   | F8 | 5.49 | n.t | 0.0124 | 1.28 | 96.64 | 1.76 | 0.014 | 0.024 |
|   | F9 | 5.42 | n.t | 0.0253 | 1.28 | 96.63 | 1.77 | 0.012 | 0.03 |
|   | F10 | 5.84 | n.t | 0.0414 | 1.33 | 96.48 | 1.82 | 0.014 | 0.018 |
| T = 6 M | F1 | 6.53 | n.t | 0.0679 | 8.36 | 82.65 | 8.5 | 0.301 | 0.542 |
| (25° C.) | F2 | 6.24 | n.t | 0.0125 | 7.17 | 84.19 | 8.17 | 0.324 | 0.399 |
|   | F3 | 6.25 | n.t | 0.0258 | 6.92 | 84.09 | 8.38 | 0.34 | 0.472 |
|   | F4 | 6.27 | n.t | 0.0383 | 6.82 | 83.83 | 8.89 | 0.345 | 0.501 |
|   | F5 | 5.88 | n.t | 0.0127 | 6.16 | 84.86 | 8.42 | 0.361 | 0.372 |
|   | F6 | 6 | n.t | 0.0291 | 5.95 | 84.22 | 9.19 | 0.405 | 0.499 |
|   | F7 | 5.81 | n.t | 0.0413 | 5.88 | 84.09 | 9.39 | 0.393 | 0.539 |
|   | F8 | 5.82 | n.t | 0.0124 | 5.31 | 84.7 | 9.3 | 0.411 | 0.455 |
|   | F9 | 5.78 | n.t | 0.0253 | 5.49 | 83.65 | 10.39 | 0.423 | 0.55 |
|   | F10 | 5.71 | n.t | 0.0414 | 5.48 | 83.3 | 10.52 | 0.425 | 0.609 |
| T = 9 M | F1 | 6.61 | n.t | 0.0675 | 1.91 | 96.19 | 1.62 | 0.01 | 0 |
| (5° C.) | F2 | 6.14 | n.t | 0.0119 | 1.72 | 96.39 | 1.65 | 0.01 | 0.01 |
|   | F3 | 6.42 | n.t | 0.0258 | 1.73 | 96.33 | 1.66 | 0.01 | 0.01 |
|   | F4 | 6.01 | n.t | 0.0396 | 1.71 | 96.35 | 1.65 | 0.02 | 0.01 |
|   | F5 | 6.17 | n.t | 0.0116 | 1.6 | 96.37 | 1.73 | 0.02 | 0.02 |
|   | F6 | 6.46 | n.t | 0.0262 | 1.61 | 96.34 | 1.75 | 0.02 | 0.02 |
|   | F7 | 5.92 | n.t | 0.0392 | 1.59 | 96.36 | 1.73 | 0.02 | 0.02 |
|   | F8 | 5.4 | n.t | 0.0119 | 1.47 | 96.27 | 1.83 | 0.02 | 0.02 |
|   | F9 | 5.98 | n.t | 0.026 | 1.47 | 96.24 | 1.85 | 0.03 | 0.02 |
|   | F10 | 5.74 | n.t | 0.0404 | 1.47 | 96.29 | 1.83 | 0.03 | 0.02 |
| T = 12 M | F1 | 7.27 | n.t | 0.0701 | 2.03 | 96.04 | 1.59 | 0 | 0.02 |
| (5° C.) | F2 | 7.09 | n.t | 0.0117 | 1.77 | 96.26 | 1.63 | 0.01 | 0.01 |
|   | F3 | 7.39 | n.t | 0.0264 | 1.77 | 96.23 | 1.64 | 0.02 | 0.01 |
|   | F4 | 6.72 | n.t | 0.0403 | 1.76 | 96.23 | 1.66 | 0.02 | 0.01 |
|   | F5 | 6.37 | n.t | 0.0118 | 1.72 | 96.3 | 1.71 | 0.02 | 0.01 |
|   | F6 | 6.71 | n.t | 0.0267 | 1.59 | 96.3 | 1.7 | 0.03 | 0.02 |
|   | F7 | 6.73 | n.t | 0.0399 | 1.72 | 96.29 | 1.69 | 0.03 | 0.01 |
|   | F8 | 6.2 | n.t | 0.0115 | 1.64 | 96.2 | 1.8 | 0.03 | 0.02 |
|   | F9 | 6.42 | n.t | 0.0261 | 1.63 | 96.19 | 1.79 | 0.04 | 0.02 |
|   | F10 | 7.19 | n.t | 0.0403 | 1.57 | 96.19 | 1.79 | 0.04 | 0.02 |

TABLE 7-continued

| Time-point | Formulation | Turbidity (NTU) | UV Vis mg/mL | PS 80 % (w/w) | pH | Light obscuration (#/mL) >10 μm | >25 μm | >50 μm | CE-SDS (reducing) Total particle counts | SEC [%] Purity (sum of LC and HC [%]) |
|---|---|---|---|---|---|---|---|---|---|---|
| T = 2 W | F1 | 8.12 | n.t | n.t | 6.66 | 4 | 0 | 0 | 193 | n.t |
| (40° C.) | F2 | 7.18 | n.t | n.t | 7.05 | 0 | 0 | 0 | 108 | n.t |
|  | F3 | 7.3 | n.t | n.t | 7.05 | 1 | 0 | 0 | 127 | n.t |
|  | F4 | 7.85 | n.t | n.t | 7.08 | 3 | 0 | 0 | 136 | n.t |
|  | F5 | 7.77 | n.t | n.t | 7.26 | 0 | 0 | 0 | 169 | n.t |
|  | F6 | 9.67 | n.t | n.t | 7.29 | 1 | 0 | 0 | 182 | n.t |
|  | F7 | 7.65 | n.t | n.t | 7.3 | 1 | 0 | 0 | 150 | n.t |
|  | F8 | 8.35 | n.t | n.t | 7.49 | 1 | 0 | 0 | 159 | n.t |
|  | F9 | 10 | n.t | n.t | 7.48 | 10 | 1 | 0 | 259 | n.t |
|  | F10 | 9.65 | n.t | n.t | 7.5 | 4 | 0 | 0 | 227 | n.t |
| T = 4 W | F1 | 11.6 | n.t | n.t | 6.86 | 10 | 0 | 0 | 1271 | 96.3 |
| (40° C.) | F2 | 9.63 | n.t | n.t | 7.01 | 9 | 0 | 0 | 406 | 95.4 |
|  | F3 | 9.69 | n.t | n.t | 7.03 | 17 | 0 | 0 | 666 | 95.5 |
|  | F4 | 10.1 | n.t | n.t | 7.03 | 9 | 0 | 0 | 1061 | 95.5 |
|  | F5 | 8.79 | n.t | n.t | 7.2 | 9 | 0 | 0 | 525 | 94.7 |
|  | F6 | 9.63 | n.t | n.t | 7.2 | 7 | 1 | 0 | 586 | 94.6 |
|  | F7 | 9.23 | n.t | n.t | 7.2 | 17 | 0 | 0 | 619 | 94.5 |
|  | F8 | 8.65 | n.t | n.t | 7.41 | 9 | 0 | 0 | 321 | 93.7 |
|  | F9 | 9.75 | n.t | n.t | 7.4 | 30 | 4 | 0 | 611 | 93.6 |
|  | F10 | 9.13 | n.t | n.t | 7.38 | 9 | 0 | 0 | 571 | 93.6 |
| T = 5 W | F1 | 9.79 | n.t | 0.06 | 6.81 | 3 | 0 | 0 | 156 | n.t |
| (5° C.) | F2 | 7.41 | n.t | 0.01 | 7.01 | 3 | 0 | 0 | 143 | n.t |
|  | F3 | 8.17 | n.t | 0.02 | 7.04 | 0 | 0 | 0 | 135 | n.t |
|  | F4 | 8.62 | n.t | 0.03 | 7.04 | 1 | 0 | 0 | 320 | n.t |
|  | F5 | 8.53 | n.t | 0.01 | 7.22 | 0 | 0 | 0 | 185 | n.t |
|  | F6 | 7.67 | n.t | 0.02 | 7.24 | 0 | 0 | 0 | 180 | n.t |
|  | F7 | 8 | n.t | 0.04 | 7.23 | 0 | 0 | 0 | 152 | n.t |
|  | F8 | 7.88 | n.t | 0.01 | 7.43 | 0 | 0 | 0 | 143 | n.t |
|  | F9 | 8.03 | n.t | 0.02 | 7.43 | 0 | 0 | 0 | 216 | n.t |
|  | F10 | 8.9 | n.t | 0.04 | 7.43 | 3 | 0 | 0 | 536 | n.t |
| T = 5 W | F1 | 10.7 | n.t | 0.05 | 6.84 | 0 | 0 | 0 | 427 | n.t |
| (25° C.) | F2 | 9.2 | n.t | 0.01 | 7.04 | 0 | 0 | 0 | 164 | n.t |
|  | F3 | 7.93 | n.t | 0.02 | 7.05 | 0 | 0 | 0 | 288 | n.t |
|  | F4 | 8.19 | n.t | 0.03 | 7.05 | 0 | 0 | 0 | 329 | n.t |
|  | F5 | 7.02 | n.t | 0.01 | 7.24 | 0 | 0 | 0 | 231 | n.t |
|  | F6 | 8.25 | n.t | 0.02 | 7.25 | 0 | 0 | 0 | 187 | n.t |
|  | F7 | 9.6 | n.t | 0.03 | 7.24 | 1 | 0 | 0 | 176 | n.t |
|  | F8 | 12.4 | n.t | 0.01 | 7.44 | 0 | 0 | 0 | 120 | n.t |
|  | F9 | 10.1 | n.t | 0.02 | 7.46 | 0 | 0 | 0 | 275 | n.t |
|  | F10 | 14.7 | n.t | 0.03 | 7.45 | 0 | 0 | 0 | 211 | n.t |
| T = 3 M | F1 | 7.15 | 119.1 | 0.0725 | 6.81 | 1 | 0 | 0 | 183 | n.t |
| (5° C.) | F2 | 7.47 | 118.2 | 0.0125 | 7.01 | 0 | 0 | 0 | 327 | n.t |
|  | F3 | 5.99 | 120.4 | 0.0265 | 7.03 | 0 | 0 | 0 | 202 | n.t |
|  | F4 | 5.81 | 120.6 | 0.0405 | 7.03 | 2 | 1 | 0 | 219 | n.t |
|  | F5 | 6.32 | 118.9 | 0.0125 | 7.23 | 1 | 0 | 0 | 160 | n.t |
|  | F6 | 5.97 | 118.2 | 0.0279 | 7.24 | 1 | 0 | 0 | 179 | n.t |
|  | F7 | 5.85 | 118.4 | 0.0396 | 7.22 | 3 | 0 | 0 | 684 | n.t |
|  | F8 | 5.71 | 118.5 | 0.0129 | 7.44 | 1 | 0 | 0 | 231 | n.t |
|  | F9 | 6.12 | 117.2 | 0.0279 | 7.44 | 1 | 0 | 0 | 236 | n.t |
|  | F10 | 6.49 | 120.8 | 0.0418 | 7.44 | 0 | 0 | 0 | 238 | n.t |
| T = 3 M | F1 | 6.57 | 121.5 | 0.0675 | 6.8 | 1 | 0 | 0 | 331 | n.t |
| (25° C.) | F2 | 6.01 | 121.1 | 0.0122 | 7.05 | 3 | 0 | 0 | 175 | n.t |
|  | F3 | 5.94 | 120.3 | 0.0268 | 7.06 | 0 | 0 | 0 | 234 | n.t |
|  | F4 | 6.35 | 119.1 | 0.0406 | 7.06 | 0 | 0 | 0 | 352 | n.t |
|  | F5 | 6.06 | 119.7 | 0.0123 | 7.23 | 0 | 0 | 0 | 451 | n.t |
|  | F6 | 5.7 | 118.3 | 0.0268 | 7.25 | 3 | 0 | 0 | 239 | n.t |
|  | F7 | 6.31 | 120.4 | 0.0404 | 7.26 | 1 | 0 | 0 | 299 | n.t |
|  | F8 | 5.41 | 120.5 | 0.0122 | 7.46 | 0 | 0 | 0 | 216 | n.t |
|  | F9 | 5.37 | 121.5 | 0.026 | 7.46 | 6 | 0 | 0 | 382 | n.t |
|  | F10 | 5.5 | 122.4 | 0.0406 | 7.45 | 6 | 0 | 0 | 255 | n.t |
| T = 6 M | F1 | 5.86 | n.t | 0.0679 | 6.74 | 4 | 0 | 0 | 564 | 99.5 |
| (5° C.) | F2 | 6.01 | n.t | 0.0125 | 6.97 | 1 | 0 | 0 | 379 | 99.4 |
|  | F3 | 6.04 | n.t | 0.0258 | 6.96 | 0 | 0 | 0 | 321 | 99.4 |
|  | F4 | 6.23 | n.t | 0.0383 | 6.97 | 3 | 0 | 0 | 460 | 99.4 |
|  | F5 | 5.88 | n.t | 0.0127 | 7.17 | 6 | 0 | 0 | 326 | 99.4 |
|  | F6 | 5.9 | n.t | 0.0291 | 7.17 | 0 | 0 | 0 | 379 | 99.4 |
|  | F7 | 5.85 | n.t | 0.0413 | 7.16 | 1 | 1 | 0 | 557 | 99.4 |
|  | F8 | 5.49 | n.t | 0.0124 | 7.37 | 0 | 0 | 0 | 413 | 99.2 |
|  | F9 | 5.42 | n.t | 0.0253 | 7.37 | 3 | 0 | 0 | 775 | 99.2 |
|  | F10 | 5.84 | n.t | 0.0414 | 7.39 | 0 | 0 | 0 | 382 | 99.2 |

TABLE 7-continued

| | | | | | | | | | | |
|---|---|---|---|---|---|---|---|---|---|---|
| T = 6 M (25° C.) | F1 | 6.53 | n.t | 0.0679 | 6.8 | 3 | 0 | 0 | 329 | 97 |
| | F2 | 6.24 | n.t | 0.0125 | 6.99 | 4 | 0 | 0 | 377 | 95.9 |
| | F3 | 6.25 | n.t | 0.0258 | 7.02 | 1 | 0 | 0 | 275 | 96.1 |
| | F4 | 6.27 | n.t | 0.0383 | 7.01 | 1 | 1 | 0 | 293 | 96 |
| | F5 | 5.88 | n.t | 0.0127 | 7.18 | 0 | 0 | 0 | 282 | 95 |
| | F6 | 6 | n.t | 0.0291 | 7.18 | 0 | 0 | 0 | 353 | 95.1 |
| | F7 | 5.81 | n.t | 0.0413 | 7.19 | 1 | 0 | 0 | 476 | 95.1 |
| | F8 | 5.82 | n.t | 0.0124 | 7.38 | 3 | 0 | 0 | 261 | 94.1 |
| | F9 | 5.78 | n.t | 0.0253 | 7.38 | 1 | 0 | 0 | 331 | 94.2 |
| | F10 | 5.71 | n.t | 0.0414 | 7.39 | 3 | 0 | 0 | 417 | 94 |
| T = 9 M (5° C.) | F1 | 6.61 | n.t | 0.0675 | 6.81 | 1 | 0 | 0 | 491 | n.t |
| | F2 | 6.14 | n.t | 0.0119 | 7.01 | 6 | 0 | 0 | 431 | n.t |
| | F3 | 6.42 | n.t | 0.0258 | 7.01 | 6 | 0 | 0 | 341 | n.t |
| | F4 | 6.01 | n.t | 0.0396 | 7.01 | 3 | 0 | 0 | 591 | n.t |
| | F5 | 6.17 | n.t | 0.0116 | 7.2 | 6 | 0 | 0 | 606 | n.t |
| | F6 | 6.46 | n.t | 0.0262 | 7.21 | 1 | 0 | 0 | 402 | n.t |
| | F7 | 5.92 | n.t | 0.0392 | 7.2 | 1 | 0 | 0 | 437 | n.t |
| | F8 | 5.4 | n.t | 0.0119 | 7.4 | 0 | 0 | 0 | 520 | n.t |
| | F9 | 5.98 | n.t | 0.026 | 7.4 | 3 | 0 | 0 | 472 | n.t |
| | F10 | 5.74 | n.t | 0.0404 | 7.4 | 4 | 0 | 0 | 799 | n.t |
| T = 12 M (5° C.) | F1 | 7.27 | n.t | 0.0701 | 6.76 | 1 | 0 | 0 | 485 | 99 |
| | F2 | 7.09 | n.t | 0.0117 | 7.03 | 1 | 0 | 0 | 664 | 98.8 |
| | F3 | 7.39 | n.t | 0.0264 | 7.03 | 0 | 0 | 0 | 354 | 98.8 |
| | F4 | 6.72 | n.t | 0.0403 | 7 | 8 | 1 | 0 | 424 | 98.9 |
| | F5 | 6.37 | n.t | 0.0118 | 7.2 | 1 | 0 | 0 | 360 | 98.8 |
| | F6 | 6.71 | n.t | 0.0267 | 7.22 | 4 | 0 | 0 | 675 | 98.7 |
| | F7 | 6.73 | n.t | 0.0399 | 7.2 | 8 | 0 | 0 | 510 | 98.6 |
| | F8 | 6.2 | n.t | 0.0115 | 7.4 | 1 | 0 | 0 | 711 | 98.5 |
| | F9 | 6.42 | n.t | 0.0261 | 7.4 | 1 | 0 | 0 | 488 | 98.4 |
| | F10 | 7.19 | n.t | 0.0403 | 7.4 | 0 | 0 | 0 | 393 | 98.4 |

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to processes, manufactures, compositions of matter, compounds, means, methods, and/or steps disclosed herein. The claims should not be read as limited to the described order or elements unless stated to that effect. It should be understood that various changes in form and detail may be made without departing from the scope of the appended claims.

---

What is claimed is:

1. An aqueous pharmaceutical composition comprising about 120 mg/ml of an anti-VEGF antibody comprising the sequences of SEQ ID NO: 1 and SEQ ID NO: 2, about 5.8% (w/v) sucrose, 10 mM sodium citrate, and 0.02% (w/v) polysorbate 80, wherein the pH of the composition is 7.2, and wherein the composition does not have an increase in particulate matter counts greater than 10 microns after three days of shaking stress.

2. The aqueous pharmaceutical composition according to claim 1, wherein the anti-VEGF antibody comprises the sequence of SEQ ID NO: 3 or 4.

3. The aqueous pharmaceutical composition according to claim 1, wherein the anti-VEGF antibody comprises the sequence of SEQ ID NO: 3 and 4.

4. The aqueous pharmaceutical composition of claim 1, comprising 120 mg/ml of the anti-VEGF antibody.

5. The aqueous pharmaceutical composition of claim 1, comprising 5.8% (w/v) sucrose.

6. The aqueous pharmaceutical composition of claim 1, comprising 3 mg of the anti-VEGF antibody.

7. The aqueous pharmaceutical composition of claim 1, comprising 6 mg of the anti-VEGF antibody.

8. The aqueous pharmaceutical composition of claim 1, wherein said composition is liquid.

9. A delivery device comprising the aqueous pharmaceutical composition of claim 1.

10. The delivery device of claim 9, which is a pre-filled syringe.

* * * * *